US012637479B2

(12) United States Patent
Li et al.

(10) Patent No.: US 12,637,479 B2
(45) Date of Patent: May 26, 2026

(54) LOW ENERGY GAP SMALL MOLECULE MATERIAL AND ORGANIC OPTOELECTRONIC DEVICE USING THE SAME

(71) Applicant: Raynergy Tek Incorporation, Hsinchu (TW)

(72) Inventors: Wei-Long Li, Hsinchu (TW); Chuang-Yi Liao, Hsinchu (TW); Yu-Tang Hsiao, Hsinchu (TW); Chia-Hua Tsai, Hsinchu (TW)

(73) Assignee: RAYNERGY TEK INCORPORATION, Hsinchu (TW)

(*) Notice: Subject to any disclaimer, the term of this patent is extended or adjusted under 35 U.S.C. 154(b) by 782 days.

(21) Appl. No.: 17/863,701

(22) Filed: Jul. 13, 2022

(65) Prior Publication Data

US 2023/0113502 A1 Apr. 13, 2023

Related U.S. Application Data

(60) Provisional application No. 63/230,149, filed on Aug. 6, 2021.

(51) Int. Cl.
*C07D 519/00* (2006.01)
*C07D 333/28* (2006.01)
(Continued)

(52) U.S. Cl.
CPC ......... *C07D 519/00* (2013.01); *C07D 333/28* (2013.01); *C07D 333/40* (2013.01); (Continued)

(58) Field of Classification Search
CPC .................................................... C07D 519/00
See application file for complete search history.

(56) References Cited

U.S. PATENT DOCUMENTS

2019/0051781 A1* 2/2019 Hirade .................. H10F 77/496

FOREIGN PATENT DOCUMENTS

CN 103374116 * 10/2013
CN 103374116 A * 10/2013
(Continued)

OTHER PUBLICATIONS

Japan Patent Office, Notice of 1st OA on Aug. 15, 2023.
(Continued)

*Primary Examiner* — William D Young
(74) *Attorney, Agent, or Firm* — WPAT, PC

(57) ABSTRACT

An organic optoelectronic device comprises a first electrode, a first carrier transport layer, an active layer, a second carrier transport layer and a second electrode. The first electrode is a transparent electrode. The active layer includes a low band gap small molecule material which includes a structure of Formula I:

(Formula I)

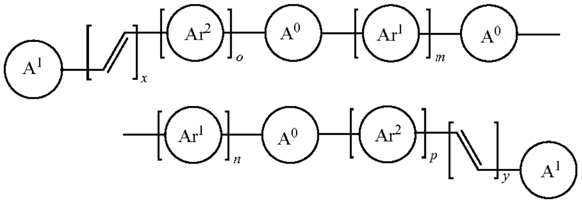

Wherein, o, m, n, p, x and y are independently selected from any integer from 0 to 2. $Ar^0$, $Ar^1$ and $A^2$ are electron-donating groups. $A^0$ is a heteroatom-containing tricyclic structure with or without substituents, and the heteroatom comprises at least one of S, N, Si, and Se. $A^1$ is an electron (Continued)

withdrawing group with or without substituents, and the structure of the electron-withdrawing group comprises at least one of S, N, Si, Se, C═O, —CN, $SO_2$. The organic optoelectronic device of the present invention has good external quantum efficiency and dark current performance.

9 Claims, 9 Drawing Sheets

(51) Int. Cl.

| | |
|---|---|
| ***C07D 333/40*** | (2006.01) |
| ***C07D 495/04*** | (2006.01) |
| ***C07D 513/04*** | (2006.01) |
| ***C07F 7/08*** | (2006.01) |
| ***C07F 7/22*** | (2006.01) |
| ***H10K 50/11*** | (2023.01) |
| ***H10K 71/30*** | (2023.01) |
| ***H10K 85/40*** | (2023.01) |
| ***H10K 85/60*** | (2023.01) |
| ***H10K 101/40*** | (2023.01) |

(52) U.S. Cl.

CPC ......... *C07D 495/04* (2013.01); *C07D 513/04* (2013.01); *C07F 7/0812* (2013.01); *C07F 7/2208* (2013.01); *H10K 50/11* (2023.02); *H10K 71/30* (2023.02); *H10K 85/40* (2023.02); *H10K 85/652* (2023.02); *H10K 85/655* (2023.02); *H10K 85/656* (2023.02); *H10K 85/657* (2023.02); *H10K 85/6572* (2023.02); *H10K 85/6576* (2023.02); *H10K 2101/40* (2023.02)

(56) References Cited

FOREIGN PATENT DOCUMENTS

| | | |
|---|---|---|
| CN | 108101930 A | 6/2018 |
| CN | 109384801 A | 2/2019 |
| CN | 112225882 A | 1/2021 |

OTHER PUBLICATIONS

Taiwan Intellectual Property Office, Notice of 2nd OA on Oct. 31, 2023.

Taiwan Intellectual Property Office, 1st OA issued on Mar. 13, 2023.

Zhang et al., "Rational design of novel A-A-D-A-A type electron donors for small molecule organic solar cells", Accepted Jun. 18, 2012, Available online Jun. 27, 2012, pp. 199-204, vol. 543, Chemical Physics Letters.

* cited by examiner

LOW ENERGY GAP SMALL MOLECULE MATERIAL AND ORGANIC OPTOELECTRONIC DEVICE USING THE SAME

The present application is based on, and claims priority from, America provisional patent application number U.S. Ser. No. 63/230,149, filed on 2021 Aug. 6, and the disclosure of which is hereby incorporated by reference herein in its entirety.

BACKGROUND OF THE INVENTION

1. Field of the Invention

The present invention relates to a low energy gap small molecule materials applied to an organic optoelectronic device, and an organic optoelectronic device including the said low energy gap small molecule materials.

2. Description of the Prior Art

In view of global warming, climate change has become a common challenge in the international communities. The Kyoto protocol proposed by the "United Nations Framework Convention on Climate Change (UNFCCC)" in 1997 which had entered into force in 2005 is aimed at reducing carbon dioxide emissions. In this regard, countries are focusing on the development of renewable energy to reduce the use of petrochemical fuels. As the sun provides far enough energy needs of people at present and for the future, renewable energy becomes a major concern for solar power generation, which has led to the use of organic optoelectronic devices for solar power generation as the primary development target.

The mainstream strategy for the preparation of high-efficiency organic optoelectronic devices is to use polymer electron donor materials and non-fullerene electron acceptor materials to construct the active layer. However, in the preparation process of polymer materials, there are usually problems such as the difficulty of precisely controlling molecular weight and dispersion, the difficulty of purifying, and poor batch stability of materials. This makes the reproducibility of the corresponding prepared organic optoelectronic devices inefficient, which is not conducive to large-scale commercial applications. In contrast, the molecular weight of small organic molecules is determined, which can be accurately synthesized, easy to purify, and has high batch-to-batch stability, which is conducive to large-scale preparation. Therefore, organic optoelectronic devices made of organic small molecule materials have high potential for commercial applications.

In recent years, organic small molecule materials, such as non-fullerene materials, have been used in organic solar cells and organic photodetectors. Because of its adjustable structure, high extinction coefficient and other advantages, it has good performance. The wavelength of visible light is in the range of 400-700 nm, while the absorption wavelength or current solar cells is in the range of 320-1100 nm, and it does not have the ability to absorb infrared light beyond 1200 nm. It can be seen from this that most of the photons of sunlight and infrared light have not yet been used and converted into electric current or signals. Therefore, the development of organic small molecular materials capable of absorbing infrared light for being applied in organic optoelectronic devices is a very important topic at present.

On the other hand, the wavelength range of organic photodetector that needs to be detected is not limited to 1000 nm. For example: the application wavelength of that needs to exceed 1000 nm in order to obtain better penetration and long-distance detection in intelligent driving and aerial photography machines application. The absorption wavelength of water is at 1350 nm, and the detector can be configured to detect the degree of moisture in food or medicine, so as to avoid accidental ingestion and affecting the human body. Light with wavelengths above 1000 nm has deeper penetration of tissue for biological detection, which can improve the contrast of the image, and the organic optoelectronic device has better flexibility, which is conducive to the production of wearable health detectors. At present, most organic small molecular materials can only absorb light with wavelengths up to 800 nm, so most of them still use organic polymer materials that can absorb wavelengths over 1000 nm as application materials. Far the above two reasons, the development of organic small molecule materials with photo response greater than 1000 nm is another very important topic at present.

SUMMARY OF THE INVENTION

In view of this, one category of the present invention is to provide a low energy gap small molecule material to break through the absorption capability of the prior art in the infrared region. According to a specific embodiment of the present invention, the low energy gap small molecule material comprises a structure of Formula I:

(Formula I)

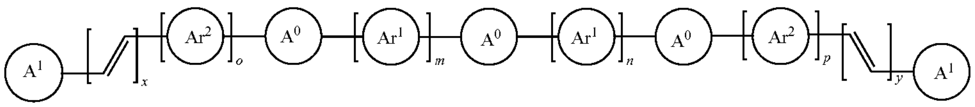

Wherein, o, m, n, p, x and y are independently selected from any integer from 0 to 2. $Ar^0$, $Ar^1$ and $Ar^2$ are electron-donating groups. $A^0$ is a tricyclic structure with or without substituents, the tricyclic structure containing heteroatom, and the heteroatom comprises at least one of S, N, Si and Se. $A^1$ is an electron-withdrawing group with or without substituents, and the structure of the electron-withdrawing group comprises at least one of S, N, Si, Se, C═O, —CN and $SO_2$.

Wherein, $Ar^0$, $Ar^1$ and $Ar^2$ are heterocyclic ring containing heteroatom, and the heteroatom comprises at least one of S, N, Si and Se.

Wherein, $Ar^0$, $Ar^1$ and $Ar^2$ in the structure of Formula I are independently selected from the group consisting of the following structures:

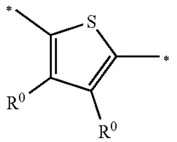

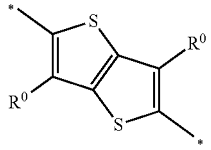

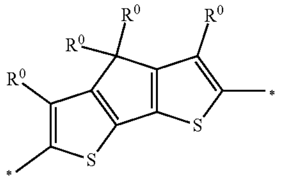

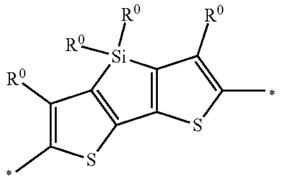

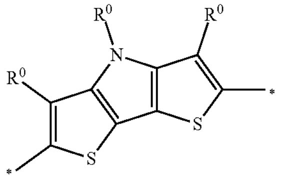

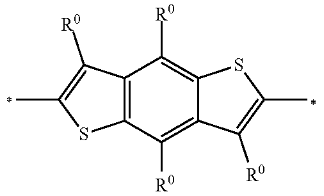

Wherein, each $R^0$ in each structure is independently selected from the group consisting of: C1-C30 alkyl, C3-C30 branched alkyl, C1-C30 silyl, C2-C30 ester, C1-C30 alkoxy, C1-C30 alkylthio, C1-C30 haloalkyl, C2-C30 olefin, C2-C30 alkyne, C2-C30 cyano-containing carbon chain, C1-C30 nitro-containing carbon chain, C1-C30 hydroxy-containing carbon chain, C3-C30 keto-containing carbon chain, halogen, cyano and hydrogen, aromatic ring with one or more $R^1$ or without substituent, heterocyclic ring with one or more $R^1$ or without substituent, fused ring with one or more $R^1$ or without substituent, fused heterocyclic ring with one or more $R^1$ or without substituent, each of $R^1$ is independently selected from the group consisting of: C1-C30 alkyl, C3-C30 branched alkyl, C1-C30 silyl, C2-C30 ester, C1-C30 alkoxy, C1-C30 alkylthio, C1-C30 haloalkyl, C2-C30 olefin, C2-C30 alkyne, C2-C30 cyano-containing carbon chain, C1-C30 nitro-containing carbon chain, C1-C30 hydroxy-containing carbon chain, C3-C30 keto-containing carbon chain, halogen, cyano and hydrogen.

Wherein, each $A^0$ in the structure of Formula 1 is independently selected from the group consisting of:

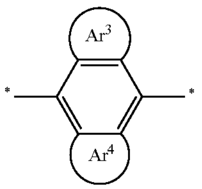

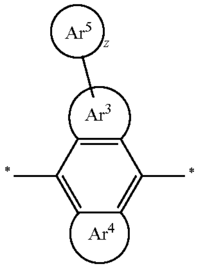

Wherein, z is any integer from 1 to 8. $Ar^3$ and $Ar^4$ are independently selected from the group consisting of: aromatic ring with one or more $R^2$ or without substituent, heterocyclic ring with one or more $R^2$ or without substituent, fused ring with one or more $R^2$ or without substituent, fused heterocyclic ring with one or more $R^2$ or without substituent. $Ar^5$ is independently selected from the group consisting of: C1-C30 alkyl, C3-C30 branched alkyl, C1-C30 silyl, C2-C30 ester, C1-C30 alkoxy, C1-C30 alkylthio, C1-C30 haloalkyl, C2-C30 olefin, C2-C30 alkyne, C2-C30 cyano-containing carbon chain, C1-C30 nitro-containing carbon chain, C1-C30 hydroxy-containing carbon chain, C3-C30 keto-containing carbon chain, halogen, cyano and hydrogen, aromatic ring with one or more $R^3$ or without substituent, heterocyclic ring with one or more $R^3$ or without substituent, fused ring with one or more $R^3$ or without substituent, fused heterocyclic ring with one or more $R^3$ or without substituent. Wherein, each of $R^2$ and $R^3$ is independently selected from the group consisting of: C1-C30 alkyl, C3-C30 branched alkyl, C1-C30 silyl, C2-C30 ester, C1-C30 alkoxy, C1-C30 alkylthio, C1-C30 haloalkyl, C2-C30 olefin, C2-C30 alkyne, C2-C30 cyano-containing carbon chain, C1-C30 nitro-containing carbon chain, C1-C30 hydroxy-containing carbon chain, C3-C30 keto-containing carbon chain, halogen, cyano and hydrogen.

Wherein, each $A^1$ in the structure of Formula 1 is independently selected from the group consisting of:

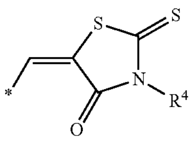

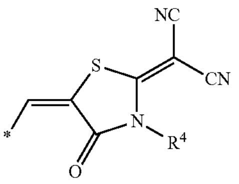

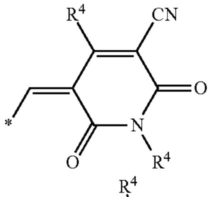

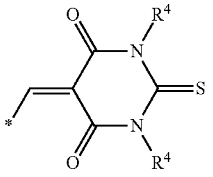

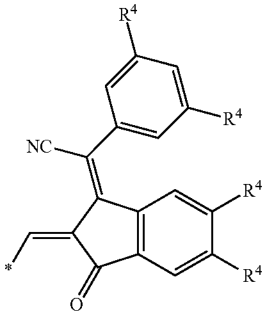

-continued
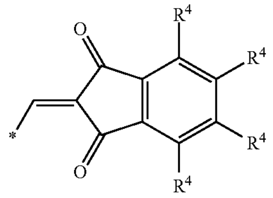
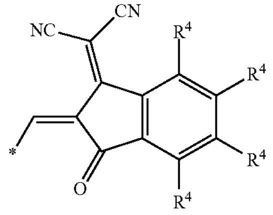
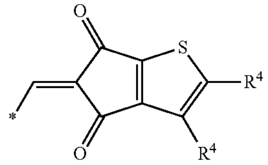
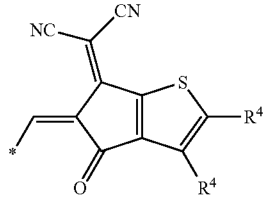
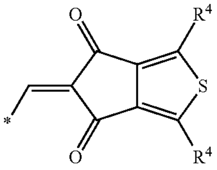
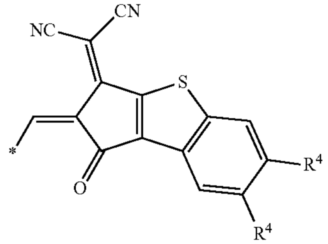
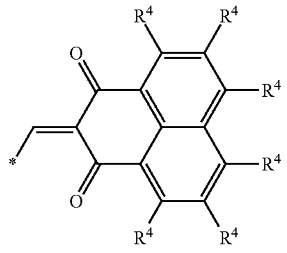
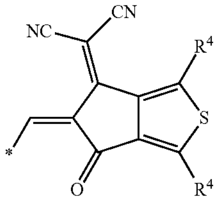
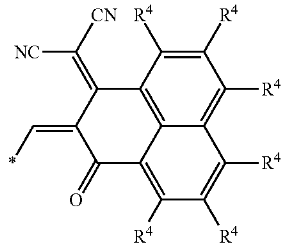
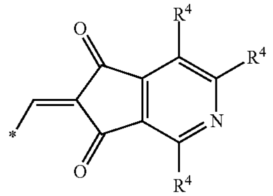
-continued
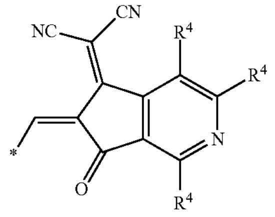
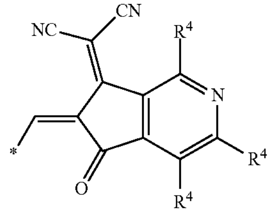
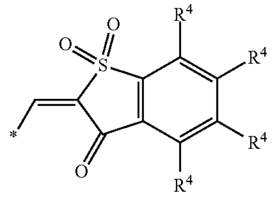
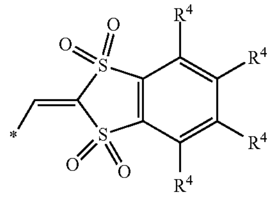
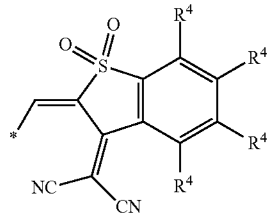
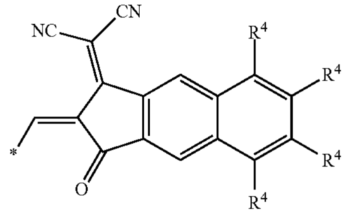
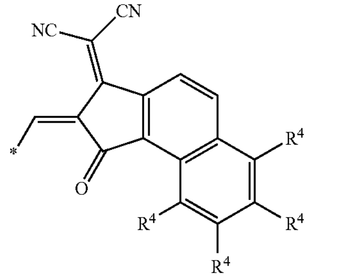

-continued

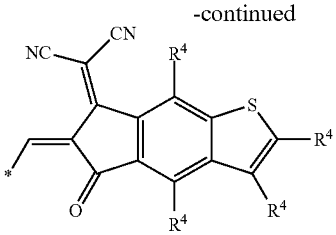

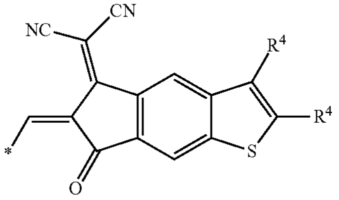

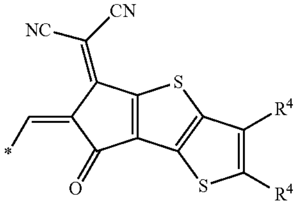

Wherein, each of $R^4$ is independently selected from the group consisting of: C1-C30 alkyl, C3-C30 branched alkyl, C1-C30 silyl, C2-C30 ester. C1-C30 alkoxy, C1-C30 alkylthio, C1-C30 haloalkyl, C2-C30 olefin, C2-C30 alkyne, C2-C30 cyano-containing carbon chain, C1-C30 nitro-containing carbon chain, C1-C30 hydroxy-containing carbon chain, C3-C30 keto-containing carbon chain, halogen, cyano and hydrogen.

In addition, "carbon chain" in this specification comprises an alkyl chain, an alkenyl chain, and an alkynyl chain.

Wherein, m=n, o=p, and x=y in the structure of Formula 1.

Wherein, $Ar^1=Ar^2$ in the structure of Formula 1.

Wherein, $m+n+o+p\neq0$ in the structure of Formula 1.

Wherein $x+y\neq0$ in the structure of Formula 1.

Another category of the present invention is to provide an organic optoelectronic device comprises a first electrode including a transparent electrode, a first carrier transport layer, an active layer which at least comprises the aforementioned low energy gap small molecule material, a second carrier transport layer and a second electrode. Wherein, the first carrier transport layer is disposed between the first electrode and the active layer, the active layer is disposed between the first carrier transport layer and the second carrier transport layer, and the second carrier transport layer is disposed between the active layer and the second electrode.

Compared with the prior art, the organic optoelectronic device made of the low energy gap small molecule material of the present invention has good absorption in the infrared region, and also has good performance of external quantum efficiency (EQE) and dark current.

BRIEF DESCRIPTION OF THE APPENDED DRAWINGS

Some of the embodiments will be described in detail, with reference to the following figures, wherein like designations denote like members, wherein.

Figure 1:
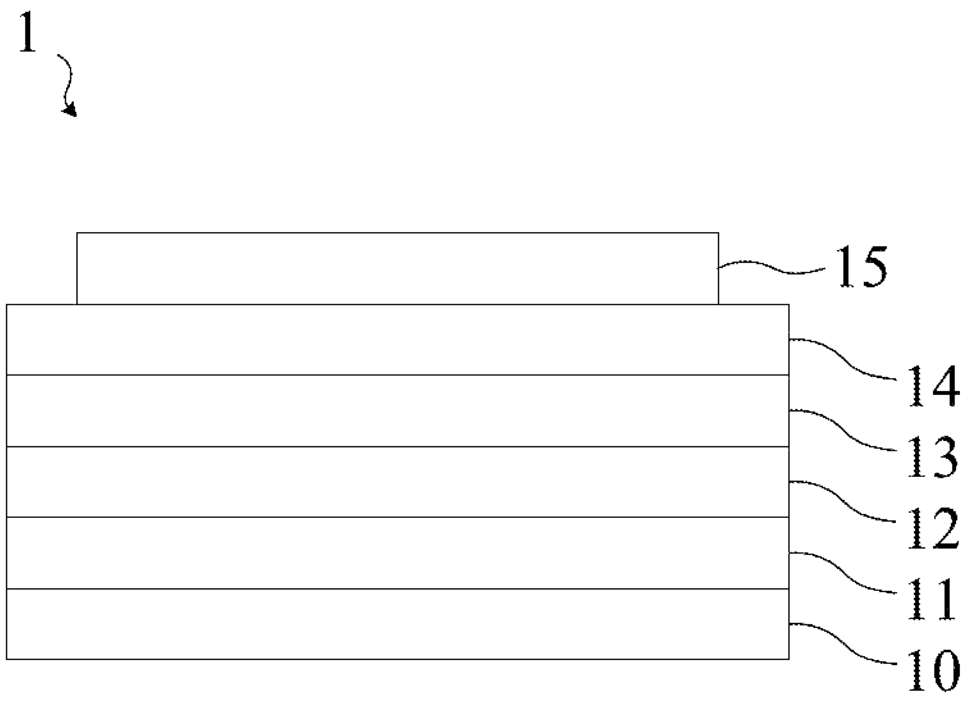
FIG. 1 shows a schematic structural diagram of one embodiment of an organic optoelectronic device of the present invention.

The advantages, spirits, and features of the present invention will be explained and discussed with embodiments and figures as follows.

DETAILED DESCRIPTION OF THE INVENTION

In order to make the advantages, spirit and features of the present invention easier and clearer, it will be detailed and discussed in the following with reference to the embodiments and the accompanying drawings. It is worth noting that the specific embodiments are merely representatives of the embodiments of the present invention, but it can be implemented in many different forms and is not limited to the embodiments described in this specification. Rather, these embodiments are provided so that this disclosure will be thorough and complete.

The terminology used in the various embodiments disclosed in the present invention is only for the purpose of describing specific embodiments, and is not intended to limit the various embodiments disclosed in the present invention. As used herein, singular forms also include plural forms unless the context clearly indicates otherwise. Unless otherwise defined, all terms (including technical and scientific terms) used in this specification have the same meanings as commonly understood by one of ordinary skill in the art to which the various embodiments disclosed herein belong. The above terms (such as those defined in commonly used dictionaries) will be interpreted as having the same meaning as the contextual meaning in the same technical field, and will not be interpreted as having an idealized or overly formal meaning, unless explicitly defined in the various embodiments disclosed herein.

In the description of this specification, the description of the reference terms "an embodiment", "a specific embodiment" and the like means that specific features, structures, materials, or characteristics described in connection with the embodiment are included in at least one embodiment of the present invention. In this specification, the schematic expressions of the above terms do not necessarily refer to the same embodiment. Furthermore, the particular features, structures, materials, or characteristics described may be combined in any suitable manner in any one or more embodiments.

Definition

The compound as used herein is considered as "environmentally stable" or "stabilized under ambient conditions" and refers to that the carrier mobility of the transistor of the semiconductor material utilized the compound is maintained at initial value while the transistor has been exposed to an environmental condition such as air, environmental temperature and humidity for a duration. For example, a compound may be considered to be environmentally stable if the change in carrier mobility of a transistor incorporating the compound is less than 20% or 10% of the initial value after being exposed to the environmental conditions including air, humidity and temperature for 3, 5 or 10 days.

The external quantum efficiency (EQE) as used herein is the spectral response Amp/Watt unit. Convert Amp to the number of electrons per unit time (electron/sec) and Watt to convert the number of photons per unit time (Photons/sec), and insert the quantum efficiency obtained by the above formula. Generally speaking, quantum efficiency (QE) refers to external quantum efficiency (EQE), also known as incident photon-electron conversion efficiency (IPCE).

The member (e.g., a thin film layer) as used herein can be considered as "photoactive" if it contains one or more compounds capable of absorbing photons to generate excitons for producing photocurrents.

As used herein, "solution proceeding" refers to a process in which a compound (e.g., a polymer), material, or composition can be used in a solution state, such as spin coating, printing (e.g., inkjet printing, gravure printing, and lithography printing), spray coating, slit coating, drop casting, dip coating, and knife coating.

As used herein, "annealing" refers to a post-deposition heat treatment to a semi-crystalline polymer film for certain duration in the environment or under decompressed or pressurized environment. "Annealing temperature" refers to the temperature at which the polymer film or the mixed film of the polymer and other molecules can perform small-scale molecular movement and rearrangement during the annealing process. Without limitation by any particular theory, it is believed that annealing can lead to an increase in crystallinity in the polymer film, enhance the material carrier mobility of the polymer film or a mixed film of the polymer with other molecules, and the molecules are arranged alternately to achieve the effect of independent transmission paths of effective electrons and holes.

As used herein, "carbon chain" refers to a line of connected carbon atoms. "Carbon chain" in this specification comprises an alkyl chain, an alkenyl chain, and an alkynyl chain.

In the current technology, the organic polymer structure with "electron donor-π-electron acceptor" structure design is mostly utilized to achieve the ability to absorb near-infrared light. Other technology uses organic small molecule structure with "electron donor-electron acceptor-electron donor" concept is designed to achieve the ability to absorb the light in 600-800 nm. The invention provides a low energy gap small molecule material. The concept of molecular structure design is that the outer structure of the low energy gap small molecule material has two strong electron-withdrawing groups, and the connected central structure is a system with π electrons or multiple electrons. Further, the molecular structure design of the present invention is $A^1$-$A^0$-$Ar^0$-$A^0$-$A^1$, wherein $Ar^0$ in the central structure can be π or a fused ring with relatively electron-donating ability, $A^0$ is a poly-fused ring, and $A^1$ in the outermost structure is a fused-ring unit with multiple electron-withdrawing groups. The present invention uses a plurality of electron-withdrawing functional groups in the structure, and such molecular structure design is easier to achieve absorption in the near-infrared wavelength band than the molecular structure design using a single strong electron-withdrawing group.

In one embodiment, the low energy gap small molecule material of the present invention comprises the following structure of Formula I:

(Formula I)

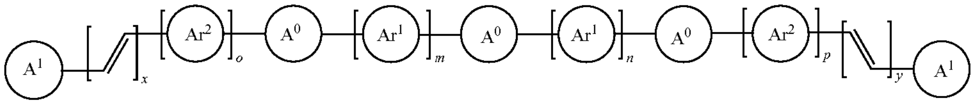

Wherein, o, m, n, p, x and y are independently selected from any integer from 0 to 2. $Ar^0$, $Ar^1$ and $Ar^2$ are electron-donating groups. $A^0$ is a tricyclic structure with or without substituents, the tricyclic structure containing heteroatom, and the heteroatom comprises at least one of S, N, Si and Se. $A^1$ is an electron-withdrawing group with or without substituents, the structure of the electron-withdrawing group comprises at least one of S, N, Si, Se, C═O, —CN and $SO_2$. In practical applications, the double bond in Formula 1 can be a double bond with or without substituents, and is not limited thereto. Wherein, the electron-withdrawing group is a group or atom with stronger electron-withdrawing ability than hydrogen, that is, it has the electron-withdrawing inductive effect. The electron-donating group is a group or atom with stronger electron-donating ability than hydrogen, that is, it has the electron-donating inductive effect. The inductive effect is the effect that the bonding electronic cloud moves in a certain direction on the atomic bond due to the different polarities (electronegativity) of the atoms or groups in the molecule. The electronic cloud prefers to move towards the group or atom with high electronegativity.

In practice, $Ar^0$, $Ar^1$ and $Ar^2$ are heterocyclic ring containing heteroatom, and the heteroatom comprises at least one of S, N, Si and Se.

In practice, $Ar^0$, $Ar^1$ and $Ar^2$ in the structure of Formula I are independently selected from the group consisting of the following structures:

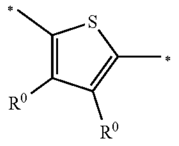

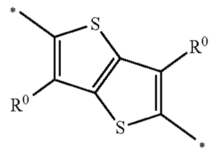

-continued

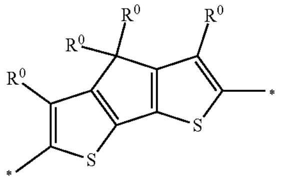

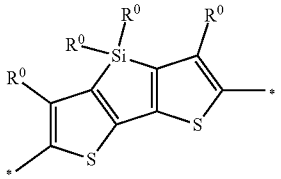

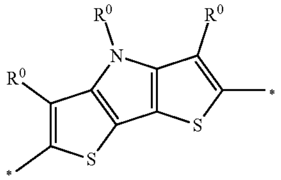

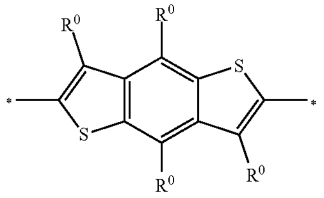

Wherein, each $R^0$ in each structure is independently selected from the group consisting of: C1-C30 alkyl, C3-C30 branched alkyl, C1-C30 silyl, C2-C30 ester, C1-C30 alkoxy, C1-C30 alkylthio, C1-C30 haloalkyl, C2-C30 olefin, C2-C30 alkyne, C2-C30 cyano-containing carbon chain, C1-C30 nitro-containing carbon chain, C1-C30 hydroxy-containing carbon chain, C3-C30 keto-containing carbon chain, halogen, cyano and hydrogen, aromatic ring with one or more $R^1$ or without substituent, heterocyclic ring with one or more $R^1$ or without substituent, fused ring with one or more $R^1$ or without substituent, fused heterocyclic ring with one or more $R^1$ or without substituent, each of $R^1$ is independently selected from the group consisting of: C1-C30 alkyl, C3-C30 branched alkyl, C1-C30 silyl, C2-C30 ester, C1-C30 alkoxy, C1-C30 alkylthio, C1-C30 haloalkyl, C2-C30 olefin, C2-C30 alkyne, C2-C30 cyano-containing carbon chain, C1-C30 nitro-containing carbon chain, C1-C30 hydroxy-containing carbon chain, C3-C30 keto-containing carbon chain, halogen, cyano and hydrogen.

In practice, each $A^0$ in the structure of Formula 1 is independently selected from the group consisting of:

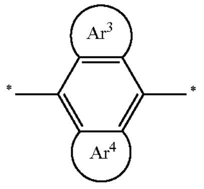

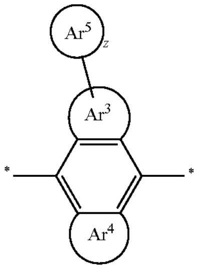

Wherein, z is any integer from 1 to 8. $Ar^3$ and $Ar^4$ are independently selected from the group consisting of: aromatic ring with one or more $R^2$ or without substituent, heterocyclic ring with one or more $R^2$ or without substituent, fused ring with one or more $R^2$ or without substituent, fused heterocyclic ring with one or more $R^2$ or without substituent. $Ar^5$ is independently selected from the group consisting of: C1-C30 alkyl, C3-C30 branched alkyl, C1-C30 silyl, C2-C30 ester, C1-C30 alkoxy, C1-C30 alkylthio, C1-C30 haloalkyl, C2-C30 olefin, C2-C30 alkyne, C2-C30 cyano-containing carbon chain, C1-C30 nitro-containing carbon chain, C1-C30 hydroxy-containing carbon chain, C3-C30 keto-containing carbon chain, halogen, cyano and hydrogen, aromatic ring with one or more $R^3$ or without substituent, heterocyclic ring with one or more $R^3$ or without substituent, fused ring with one or more $R^3$ or without substituent, fused heterocyclic ring with one or more $R^3$ or without substituent. Wherein, each of $R^2$ and $R^3$ is independently selected from the group consisting of: C1-C30 alkyl, C3-C30 branched alkyl, C1-C30 silyl, C2-C30 ester, C1-C30 alkoxy, C1-C30 alkylthio, C1-C30 haloalkyl, C2-C30 olefin, C2-C30 alkyne, C2-C30 cyano-containing carbon chain, C1-C30 nitro-containing carbon chain, C1-C30 hydroxy-containing carbon chain, C3-C30 keto-containing carbon chain, halogen, cyano and hydrogen.

In practice, each $A^1$ in the structure of Formula 1 is independently selected from the group consisting of:

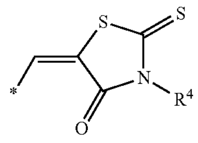

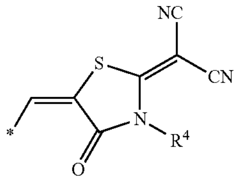

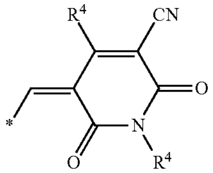

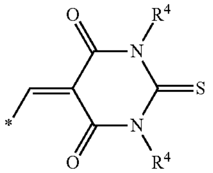

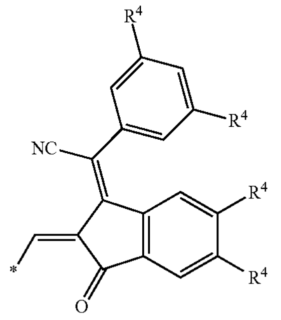

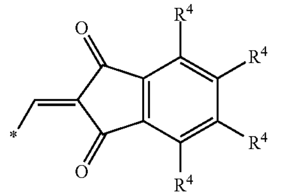

-continued
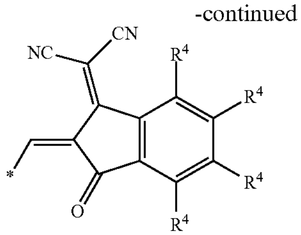
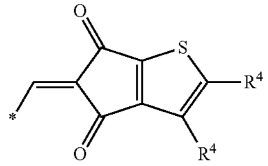
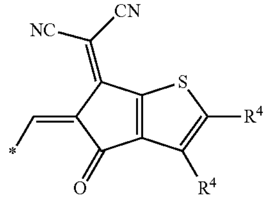
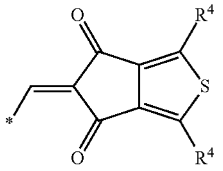
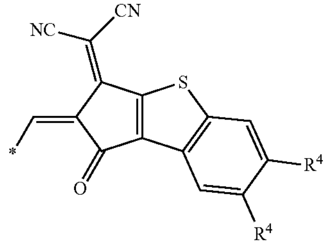
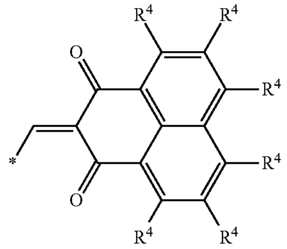
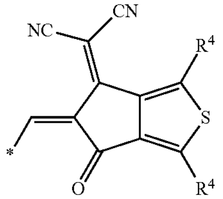
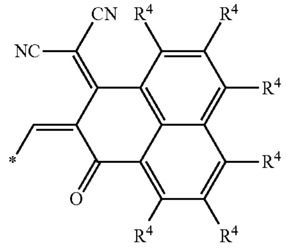
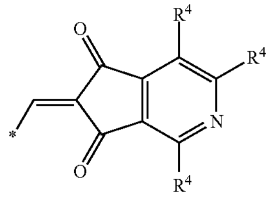
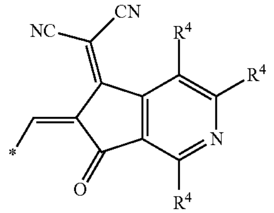
-continued
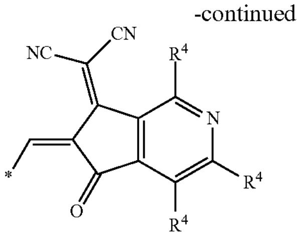
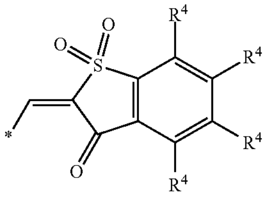
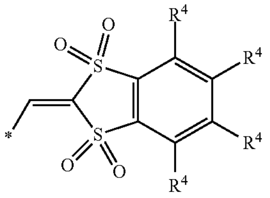
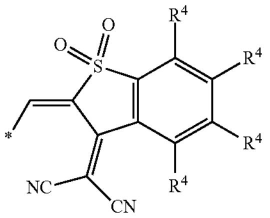
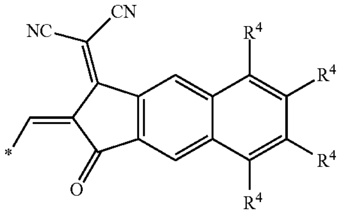
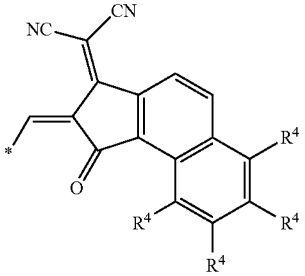
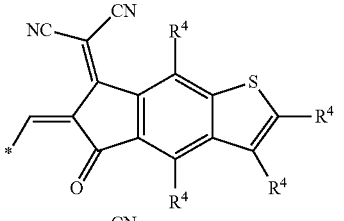
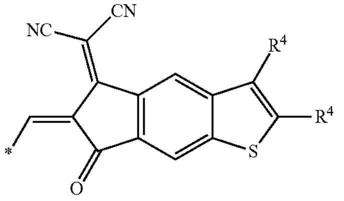

-continued

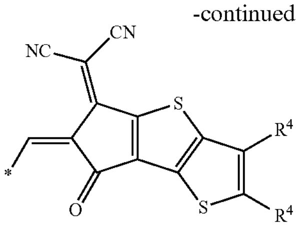

Wherein, each of $R^4$ is independently selected from the group consisting of: C1-C30 alkyl, C3-C30 branched alkyl, C1-C30 silyl, C2-C30 ester, C1-C30 alkoxy, C1-C30 alkylthio, C1-C30 haloalkyl, C2-C30 olefin, C2-C30 alkyne, C2-C30 cyano-containing carbon chain, C1-C30 nitro-containing carbon chain, C1-C30 hydroxy-containing carbon chain, C3-C30 keto-containing carbon chain, halogen, cyano and hydrogen.

In practice, the low energy gap small molecule material of the present invention can comprise the following structure:

Q1

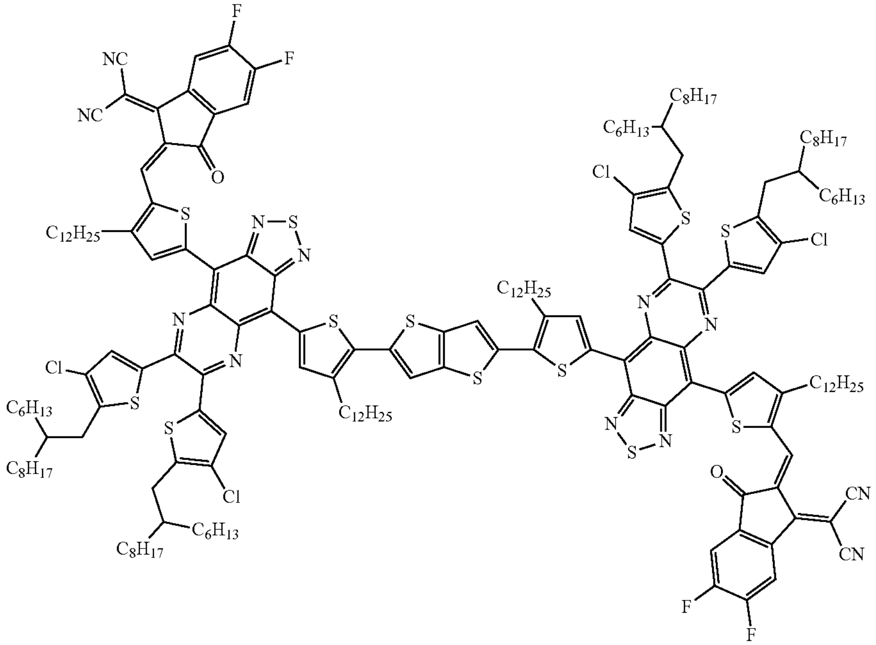

Q2

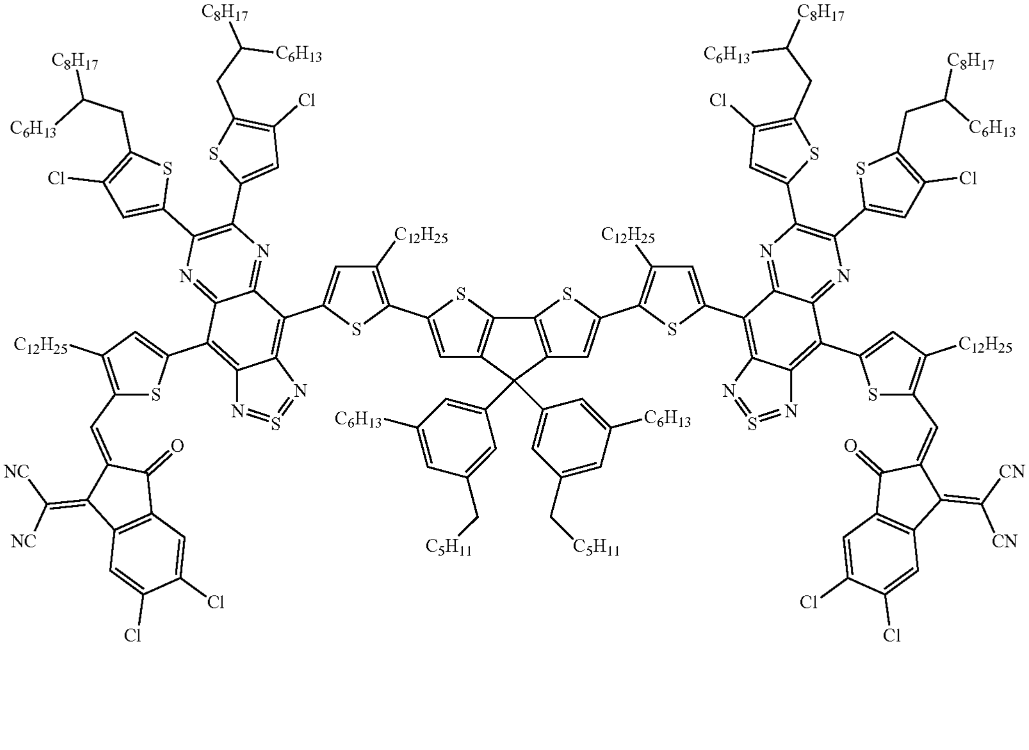

-continued
Q3
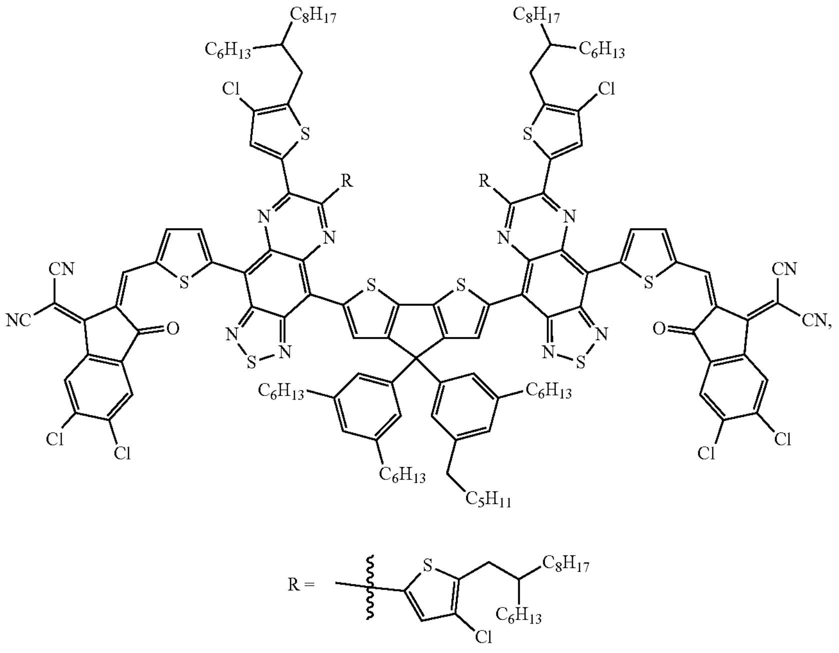
Q4
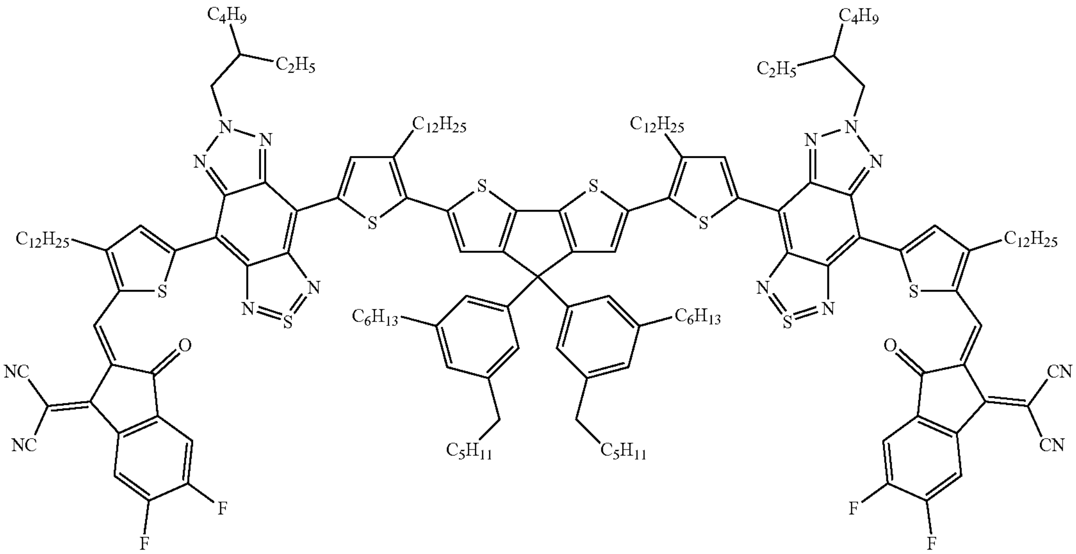

-continued
Q5
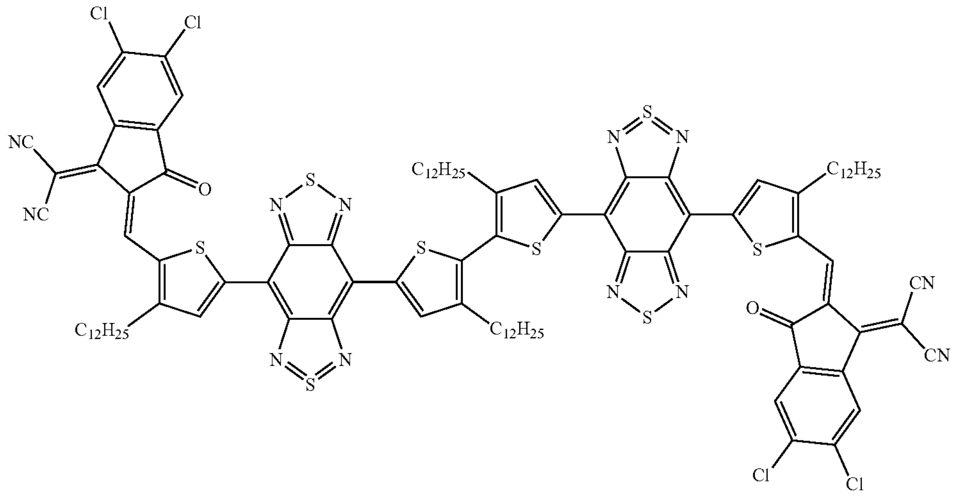
Q6
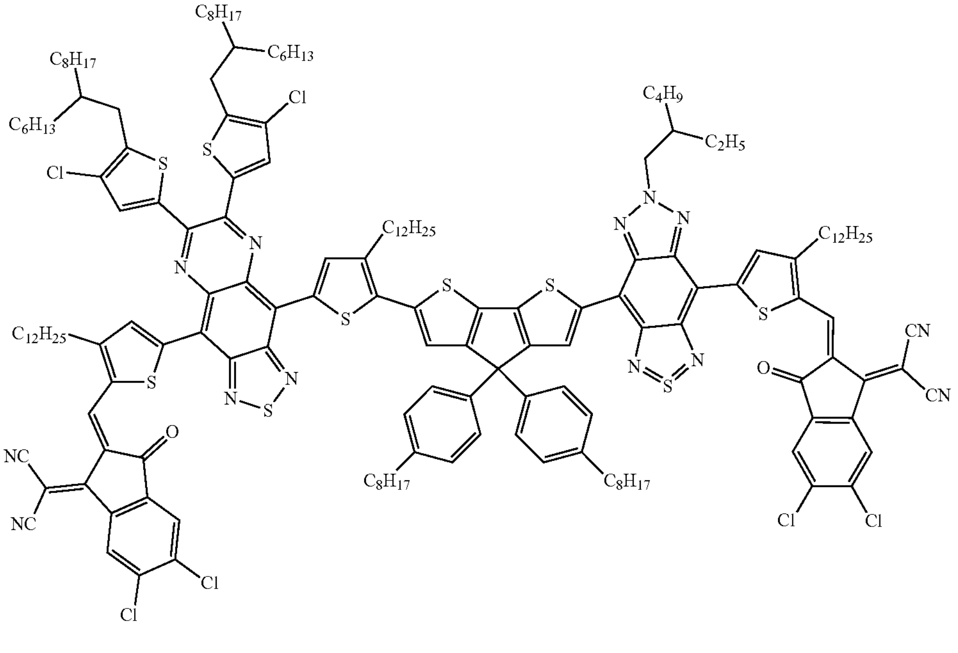

-continued
Q7
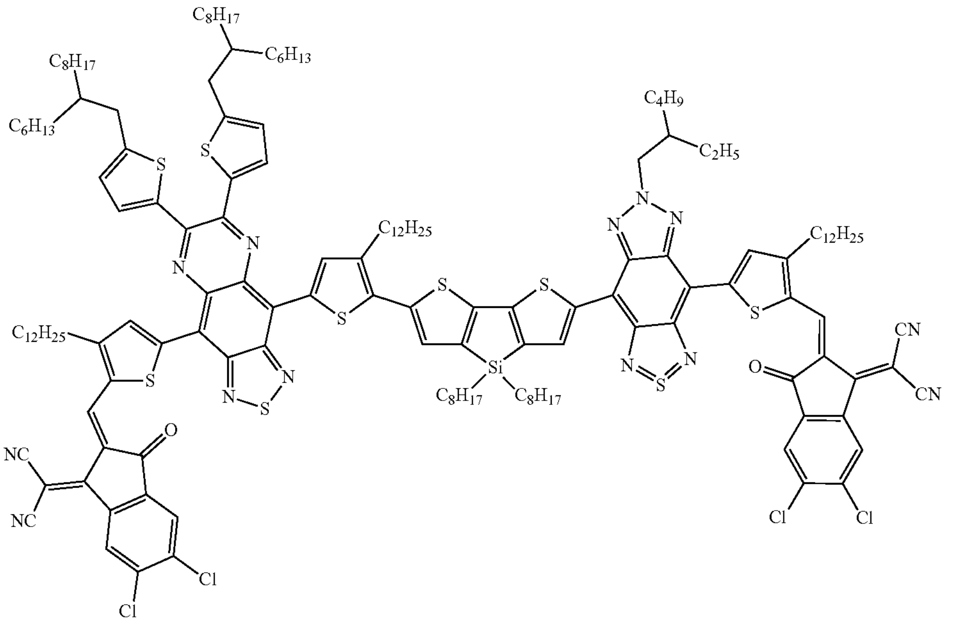
Q8
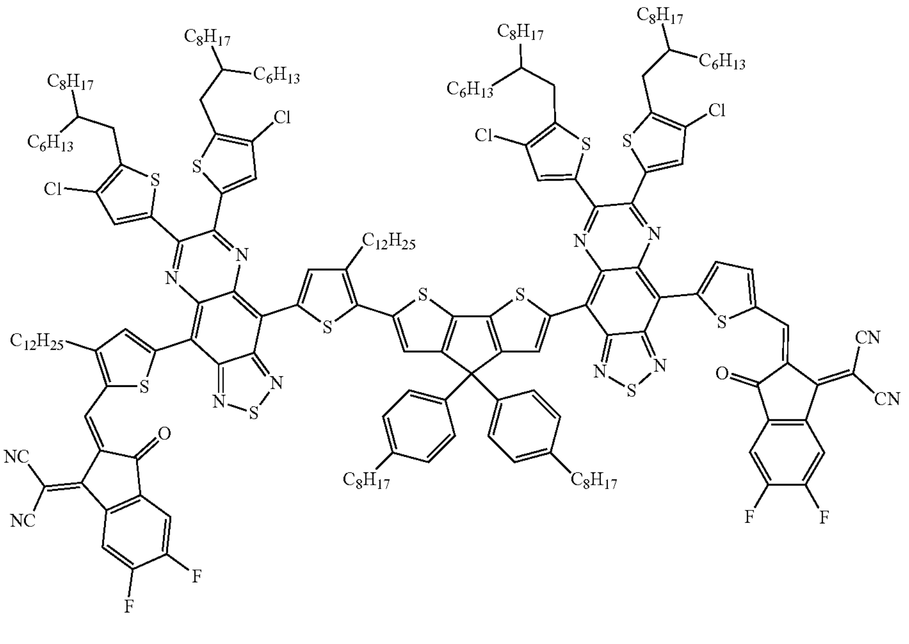

-continued
Q9
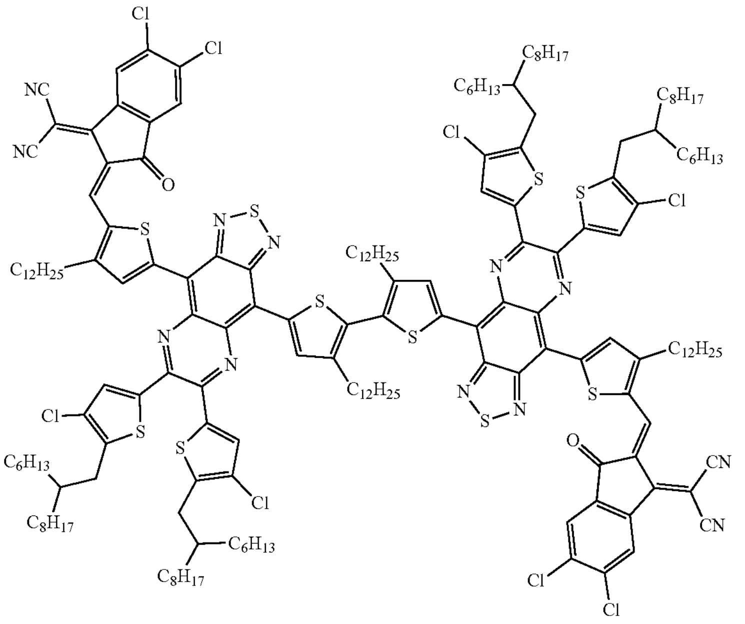
Q10
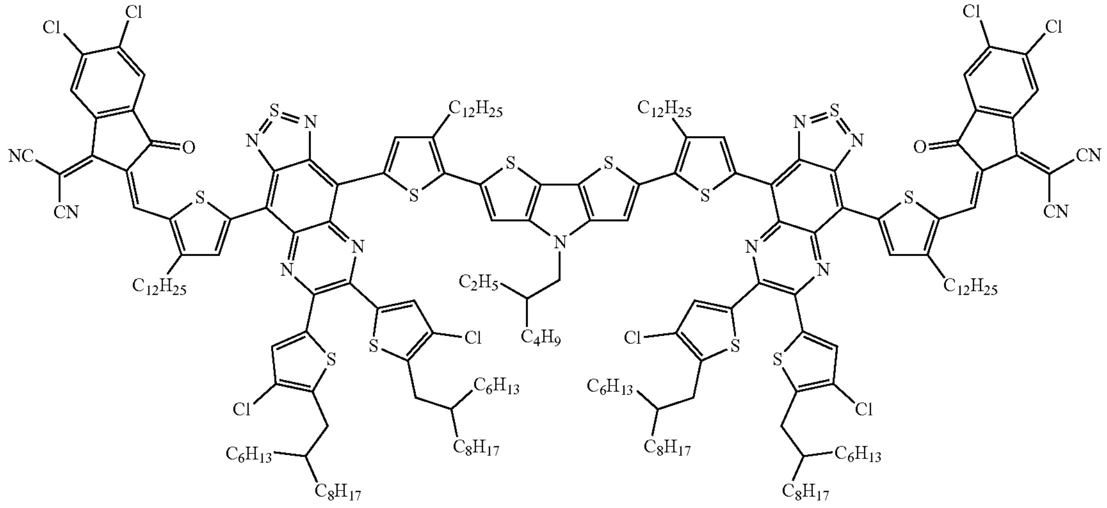

-continued
Q11
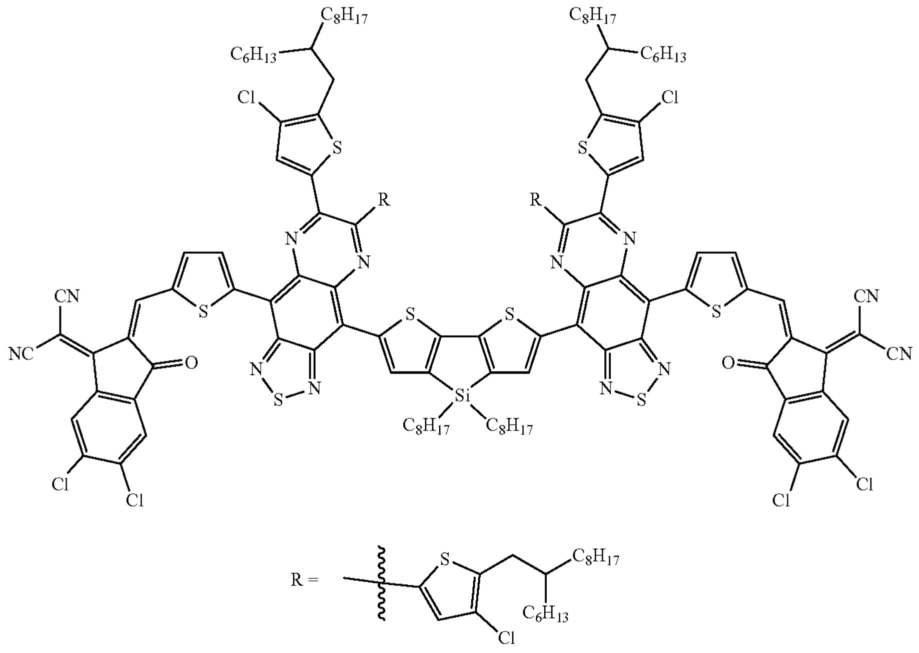
Q12
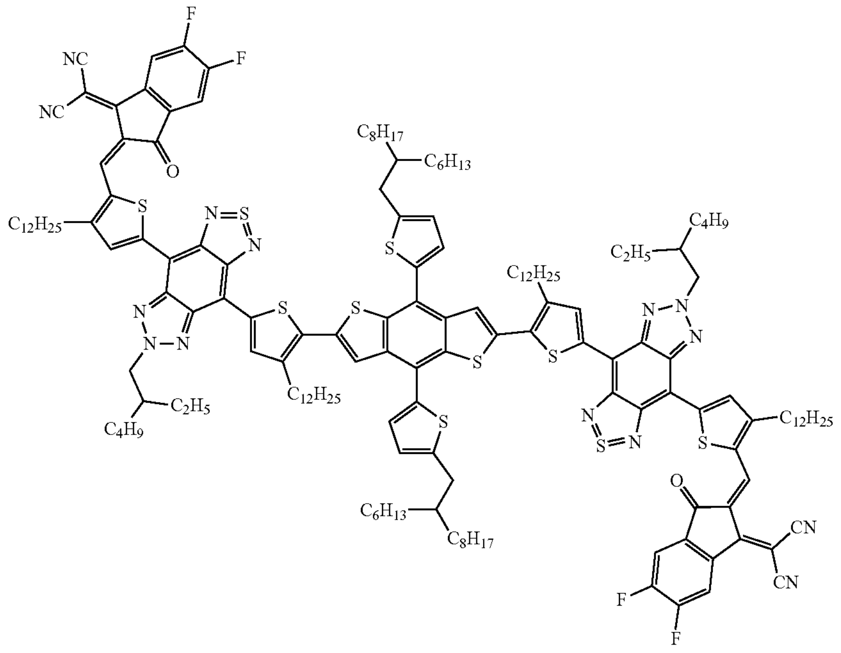

-continued
Q13
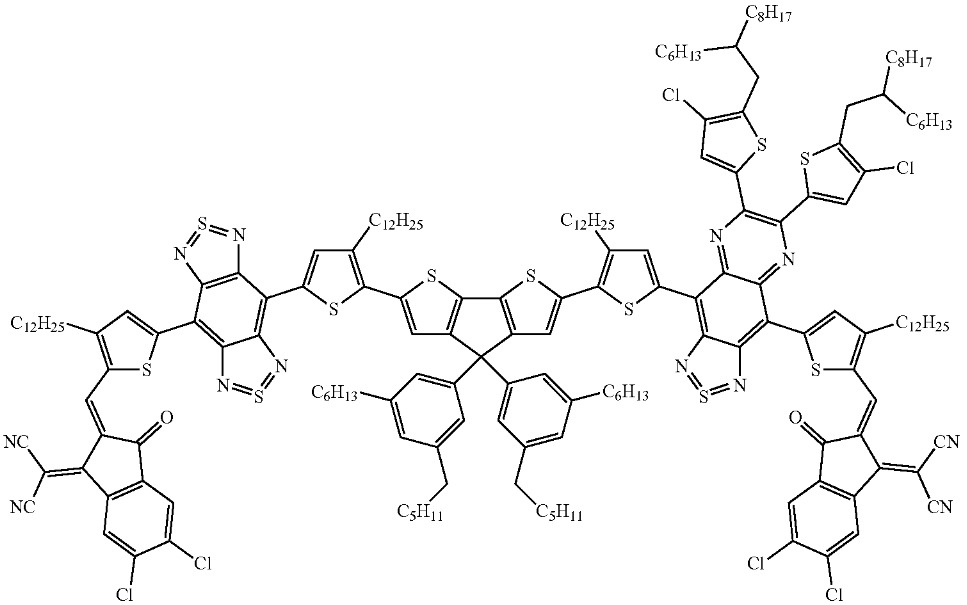
Q14
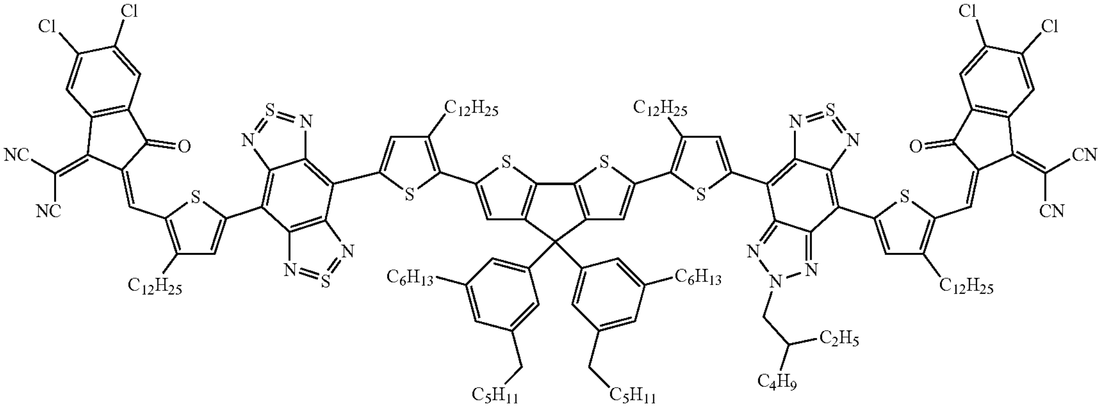
Q15
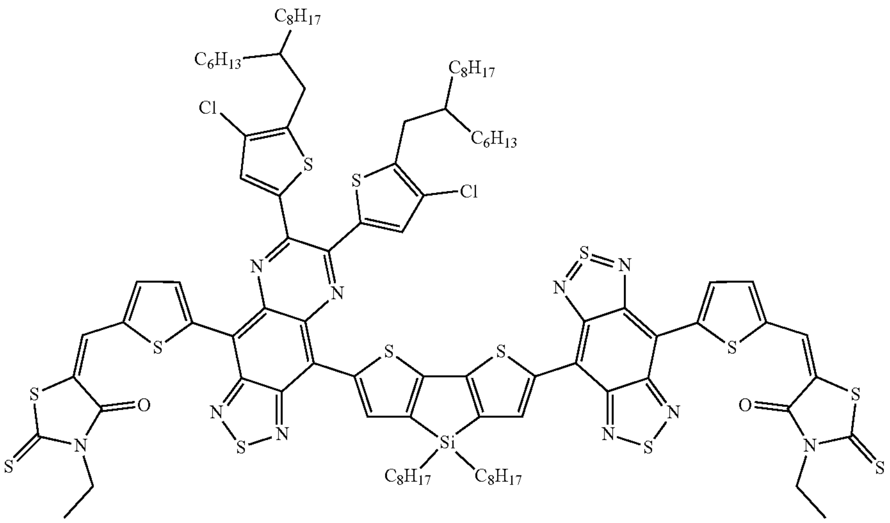

-continued
Q16
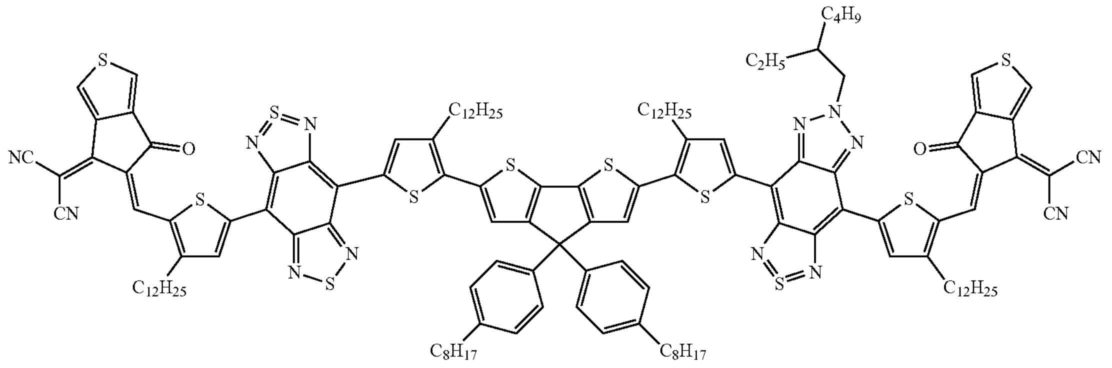
Q17
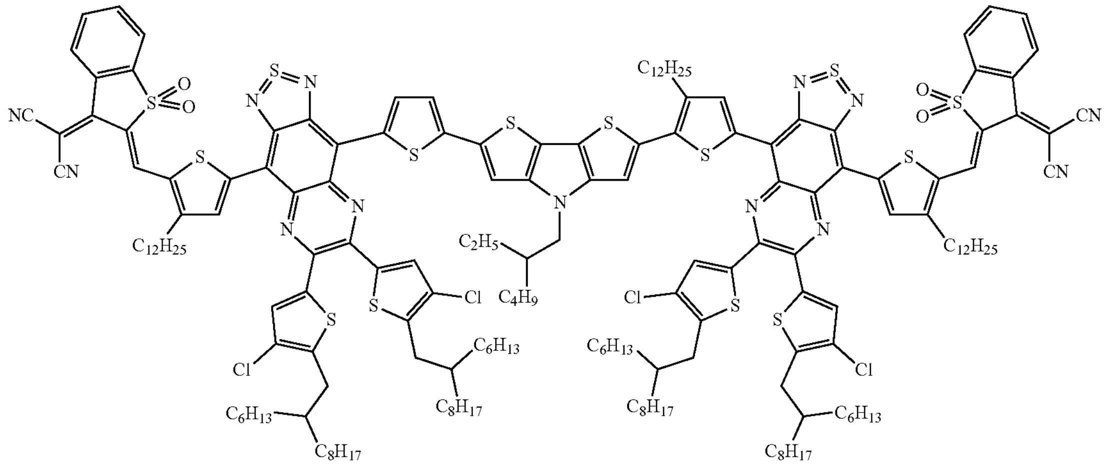
Q18
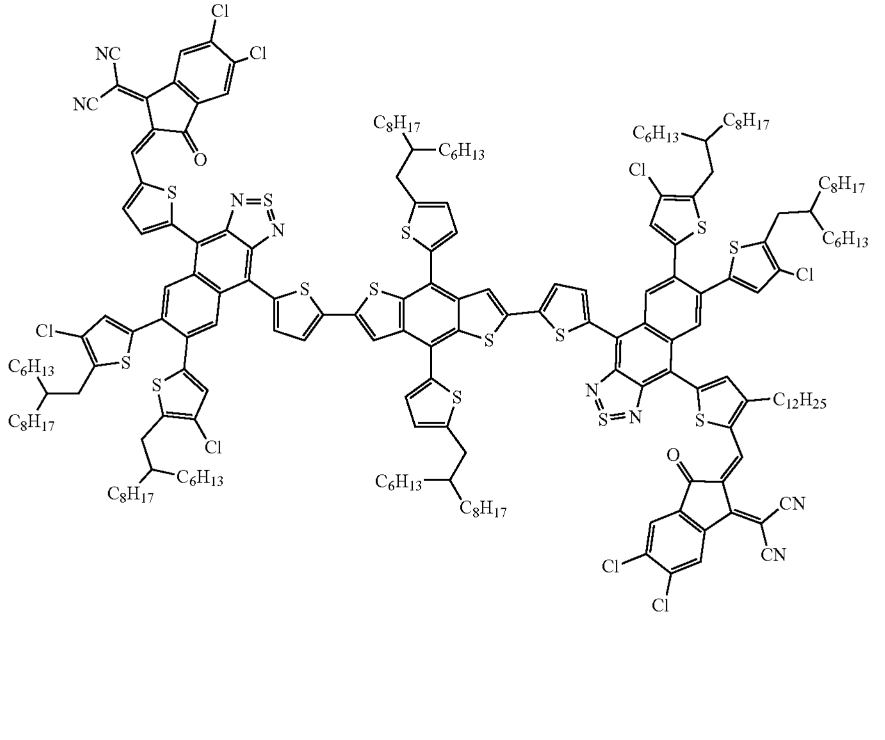

-continued
Q19
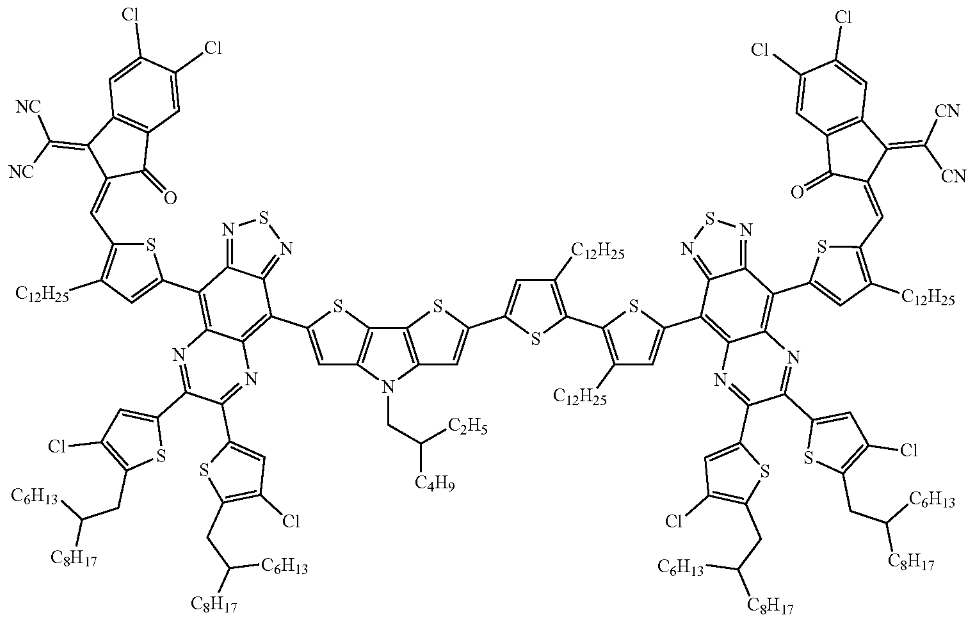
Q20
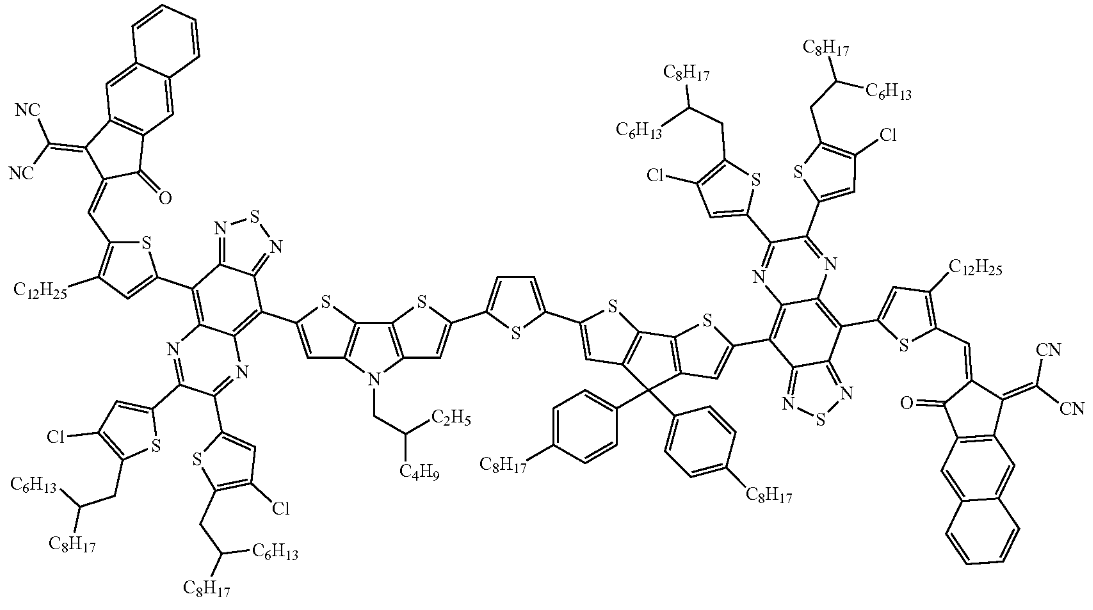

-continued
Q21
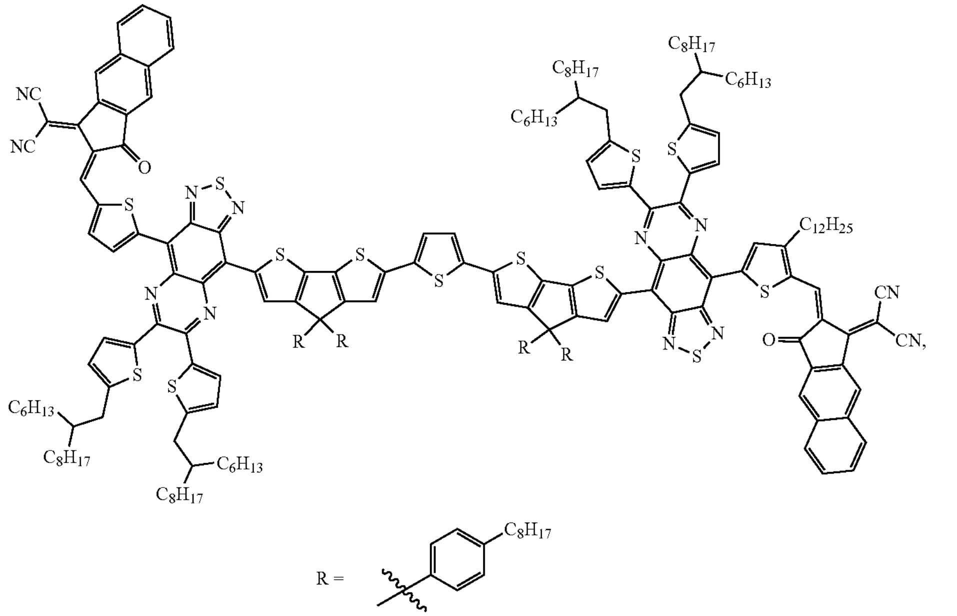
Q22
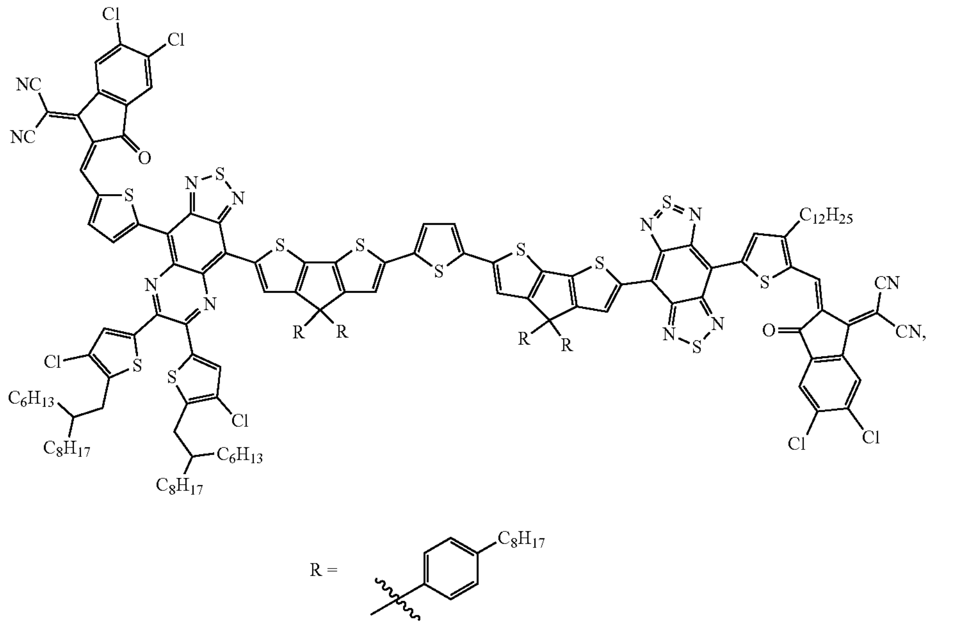

-continued
Q23
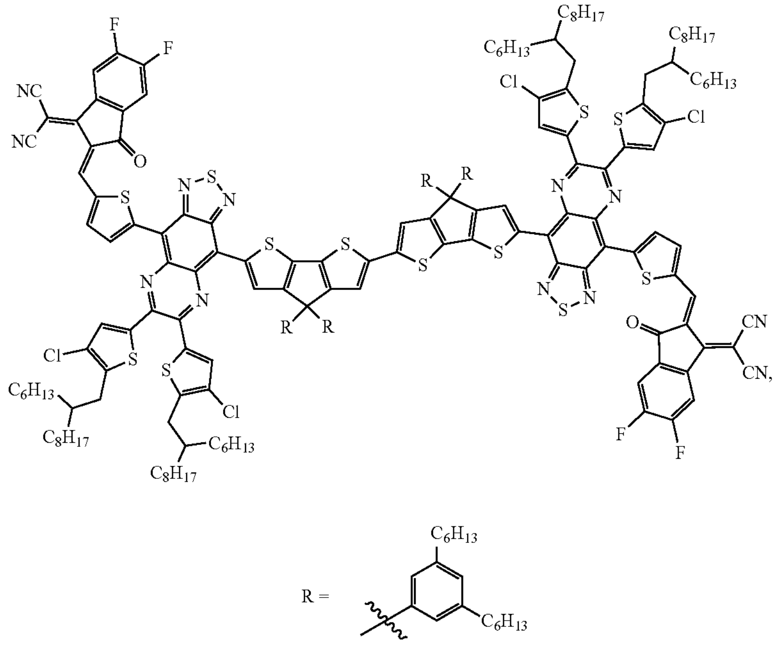
Q24
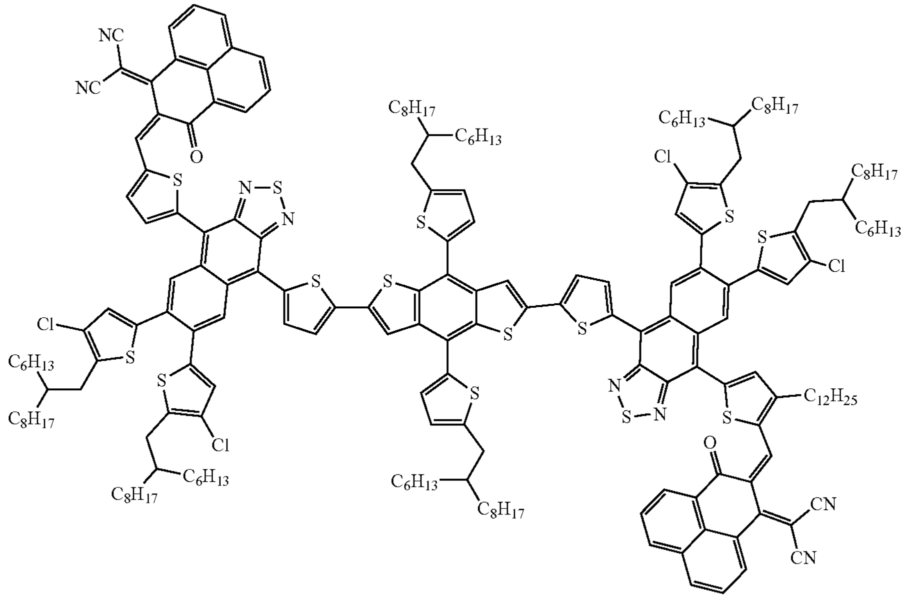

-continued
Q25
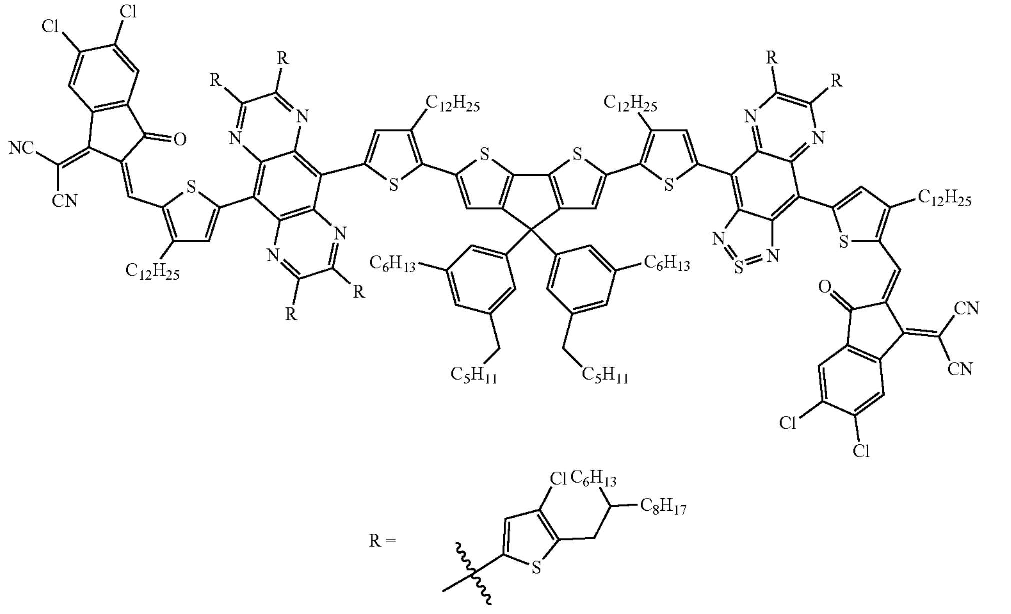
Q26
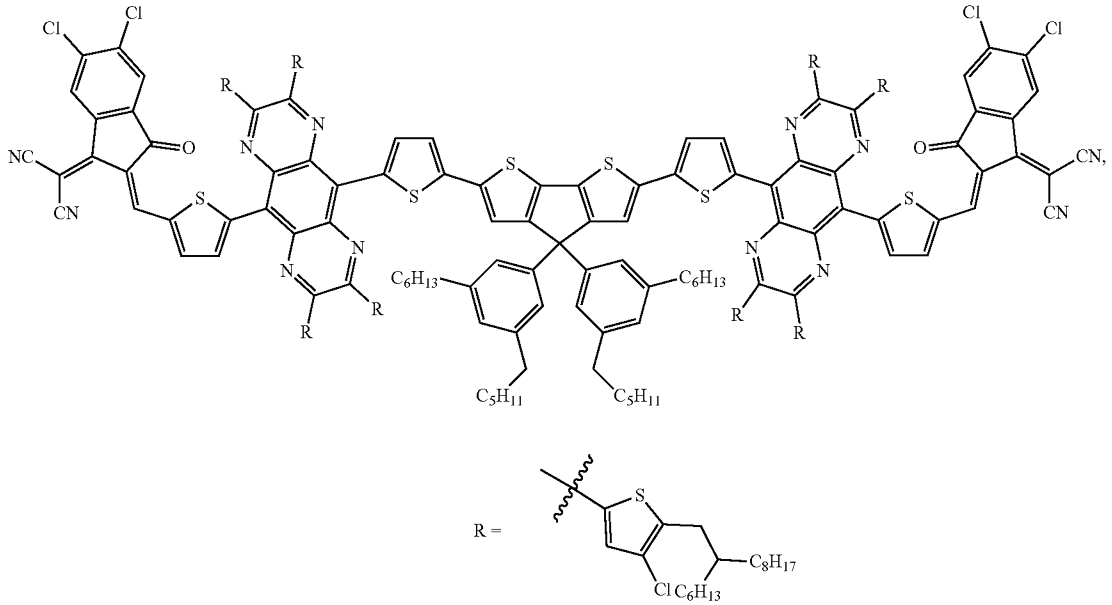

-continued

Q27

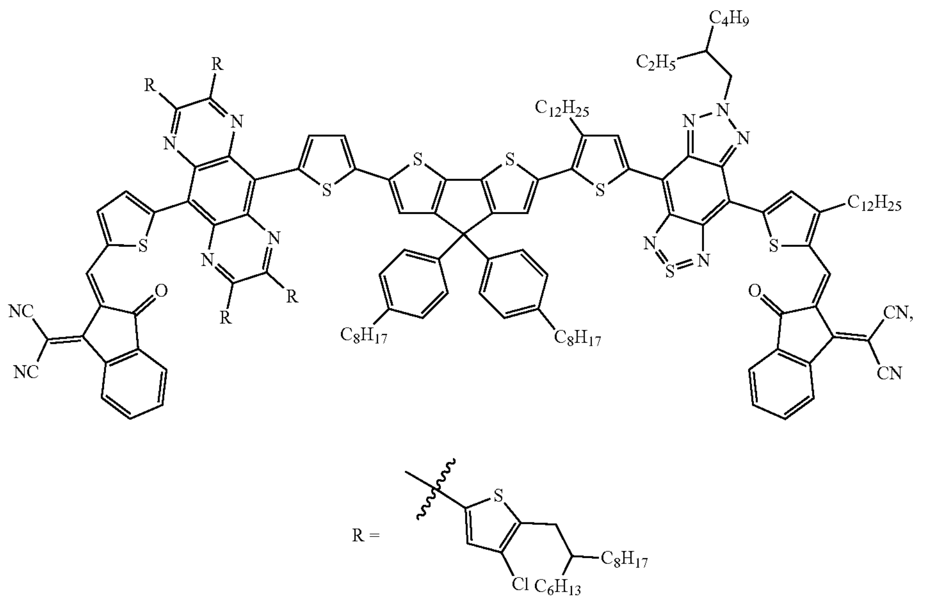

Q28

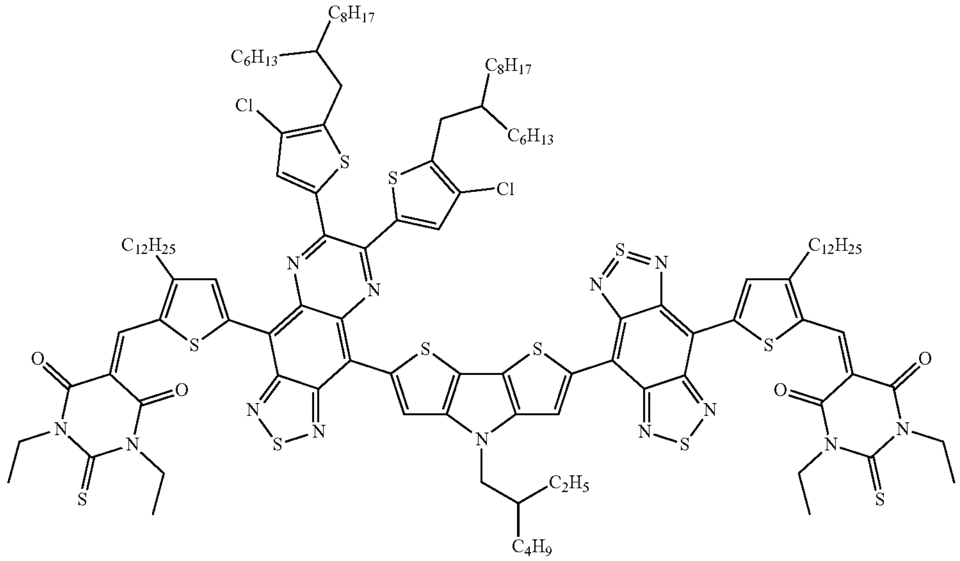

Wherein, the above-mentioned embodiment comprises at least one of the following conditions: m=n, o=p, and x=y; at least one of m≠n, o≠p, x≠y; and $Ar^1=Ar^2$; $Ar^1≠A^2$. In addition, in practice, at least one of the following conditions is included: m+n+o+p≠0 and x+y≠0. It should be understood that the above-listed embodiments are only for those skilled in the art to more clearly understand the structural composition of the present invention, and are not limited thereto.

Please refer to FIG. 1. FIG. 1 shows a schematic structural diagram of one embodiment of an organic optoelectronic device of the present invention. As shown in FIG. 1, in another embodiment, the present invention further provides an organic optoelectronic device 1, which comprises a first electrode 11, a second electrode 15 and an active layer 13. The active layer 13, which comprises the aforementioned low energy gap small molecule material, is disposed between the first electrode 11 and the second electrode 15. In practice, the organic optoelectronic device 1 may have a laminated structure, which sequentially includes a substrate 10, the first electrode 11 (transparent electrode), a first carrier transport layer 12, the active layer 13, a second carrier transport layer 14 and the second electrode 15. In addition, the organic optoelectronic device 1 may include an organic photovoltaic device, an organic photodetector device, an organic light emitting diode, and an organic thin film transistor (OTFT).

In practice, the active layer 13 of the organic optoelectronic device 1 of the present invention comprises the low energy gap small molecule material of the Formula 1 described above.

In order to illustrate the low energy gap small molecule material of the present invention more clearly, four embodiments Q1-Q4 will be used, and the low energy gap small molecule material of the present invention will be used as the N-type material of the active layer, and further prepared into organic optoelectronic devices to conduct experiments.

Preparation of the Active Layer

Synthesis of C3

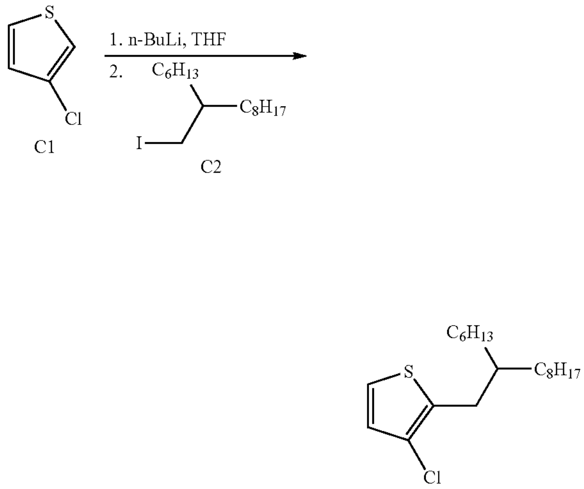

C1

C2

C3

C1 (10 g, 86.3 mmol) was placed into a 500 mL four-neck reaction flask. Under stirring, 50 mL of anhydrous THF was added to dissolve and cooled down to 15° C. 34.5 mL of n-BuLi (n-butyllithium) was added dropwise and slowly, the process is about 60 minutes, the color of solution was light orange, and the temperature did not exceed 17° C. The reaction mixture was warmed to room temperature and was stirred for 1 hour. At 15° C. C2 (19.81 g, 5.62 mmol) was added dropwise for about 2 minutes, and the color of solution was pale yellow and clear. The temperature of the reaction mixture was returned to room temperature and the reaction mixture was stirred for 20 hours. 5 mL of water was added to stop the reaction, and after the organic solvent was removed by vacuum rotary evaporator, 100 mL of heptane was added, and the mixture was extracted three times with 20 mL of water. The organic layer was taken to remove water, and the organic solvent was removed by vacuum rotary evaporator to obtain about 20 g of crude product. The starting material and impurities were removed by distillation under reduced pressure (0.25 torr, 80-100° C.). The residue (about 10 g) was purified by a silica gel column, and the eluent was heptane (about 150 mL). The main segment was collected, the organic solvent was removed, and dried under vacuum at 50° C. to obtain light yellow oil C3. Yield: 9.3 g, 51%. $^1$H NMR (500 MHz, $CDCl_3$) δ 7.09 (d, J=6.5 Hz, 1H), 6.85 (d, J=6.5 Hz, 1H), 2.72 (d, J=7.0 Hz, 2H), 1.68 (m, 1H), 1.27 (m, 24H), 0.88 (m, 6H).

Synthesis of C4

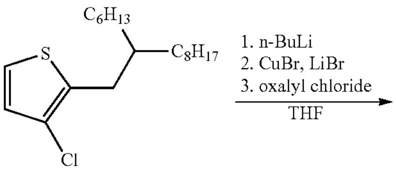

C3

-continued

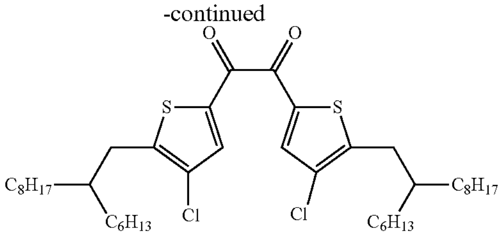

C4

C3 (20 g, 58.31 mmol) was placed into a 250 mL three-neck reaction flask. 160 mL of THF (tetrahydrofuran) was added. Under an ice bath (<10° C.), n-BuLi (23.32 mL, 58.31 mmol) was added. Keep under ice bath (<10° C.) with continuous stirring for one hour. Separately, CuBr (cuprous bromide) (8.36 g, 58.31 mmol) and LiBr (lithium bromide) (5.06 g, 58.31 mmol) were placed in another 500 mL three-neck reaction flask, and 160 mL of THF was added under an ice bath. The two reaction mixtures were mixed and stirred in an ice bath for 1 hour. Under an ice bath, oxalyl chloride (3.36 g. 2.27 mL, 26.5 mmol) was added, and the temperature of the reaction mixture was returned to room temperature and the reaction mixture was stirred for 18 hours. 100 mL of water was added to terminate the reaction, and most of the THF was removed by a vacuum rotary evaporator; 200 mL of heptane was added; and the mixture was extracted three times with 100 mL of water. The organic layers were collected to remove water and concentrated. The residue was purified by column chromatography with silica gel, and the eluent was Hep/DCM (n-heptane/dichloromethane)=4/1. The main segment was collected and concentrated to give C4 as an orange oily liquid. Yield: 12 g. 61.2%. $^1$H NMR (500 MHz, $CDCl_3$) δ 7.88 (s, 2H), 2.80 (d, J=7.0 Hz, 4H), 1.76 (m, 2H), 1.29 (m, 48H), 0.88 (m, 12H).

Synthesis of C7

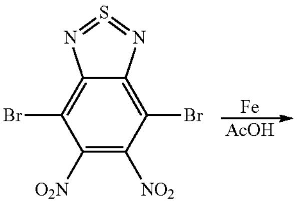

C5

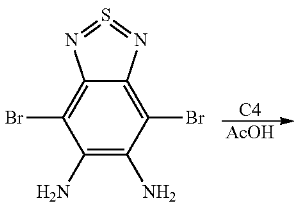

C6

-continued

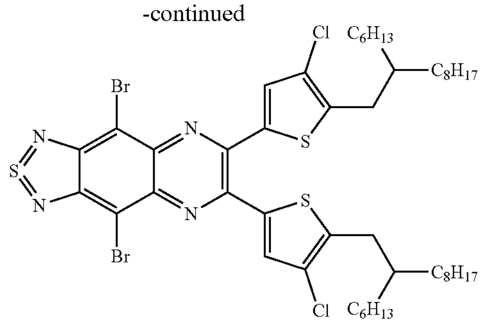

C7

C5 (2 g, 5.21 mmol) was placed into a 100 mL three-neck reaction flask. 60 mL of glacial acetic acid was added. With vigorous stirring, iron powder (5.83 g, 104.4 mmol) was added. The reaction mixture was heated to 80° C. for 16 hours. The temperature of the reaction mixture was cooled to room temperature, the reaction mixture was poured into 200 mL of ice water and filtered, the solid was rinsed with distilled water and then dried. The crude product was dissolved in 200 mL of THF and filtered to remove iron powder. The organic solution was concentrated under reduced pressure to obtain C6 and dried in vacuo. C6 intermediate was obtained, yield: 1.35 g. 80%. C4 (2.7 g, 3.65 mmol) and 40 mL of glacial acetic acid were added. Under vigorous stirring, the reaction mixture was heated to 120° C. and reacted for 16 hours. After cooling to room temperature, the reaction mixture was poured into 50 mL of ice water. The reaction mixture was extracted with DCM (dichloromethane) and washed the organic layer three times with 50 mL of distilled water. The organic layer was dehydrated with anhydrous magnesium sulfate, and concentrated under reduced pressure to obtain a crude product. The crude product was purified by column chromatography with silica gel, and the eluent is Hep/DCM (n-heptane/dichloromethane)=4/1. The main segment was collected, concentrated to obtain a dark red solid, and dried in vacuo to obtain C7. Yield: 2.4 g, 61.6%. $^1$H NMR (500 MHz, $CDCl_3$) δ 7.45 (s, 2H), 2.83 (d, J=7.0 Hz, 4H), 1.83 (m, 2H), 1.30 (m, 48H), 1.89 (m, 12H).

Synthesis of C9

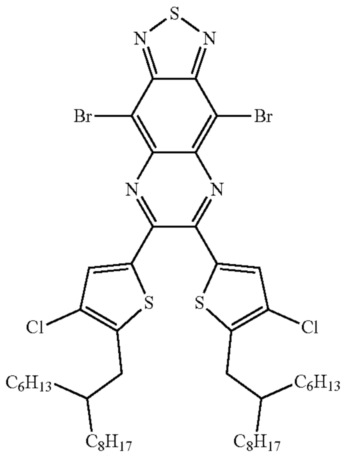

C7

+

-continued

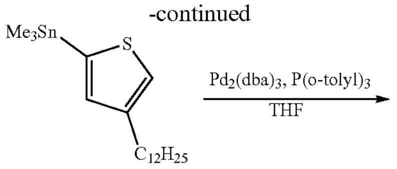

C8

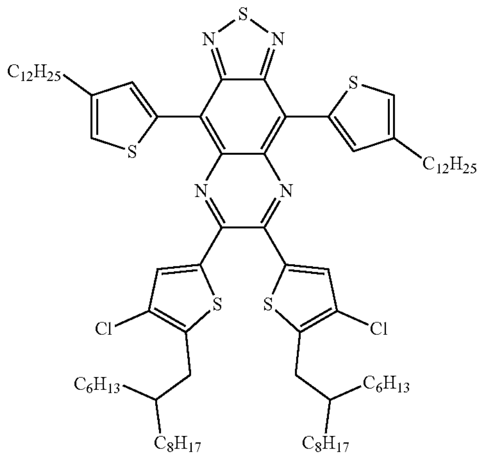

C9

C7 (1 g, 0.97 mmol) and C8 (1.05 g, 2.52 mmol) were placed in a 100 mL three-neck reaction flask, and 30 mL of THF was added. The solution was purged with argon for 15 minutes. $Pd_2(dba)_3$ (tris(dibenzylideneacetone) dipalladium) (0.036 g, 0.039 mmol) and $P(o\text{-tolyl})_3$ (tris(o-tolyl)phosphine) (0.048 g, 0.158 mmol) were added, and the reaction mixture was heated to 66° C. and stirred for 2 hours. After cooling, the reaction mixture was filtered through celite, rinsed with heptane, and removed the organic solution by a vacuum rotary evaporator. The crude product was purified by column chromatography with silica gel, and the eluent was DCM/Hep=1/9. The main segment was collected and concentrated to obtain a brown viscous liquid C9. Yield: 1.23 g, 92.2%. $^1$H NMR (500 MHz, $CDCl_3$) δ 8.70 (s, 2H), 7.40 (s, 2H), 7.29 (s, 2H), 2.83 (d, J=7.0 Hz, 4H), 2.76 (t, J=7.0 Hz), 4H), 1.76 (m, 6H), 1.42 (m, 84H), 0.85 (m, 18H).

Synthesis of C10

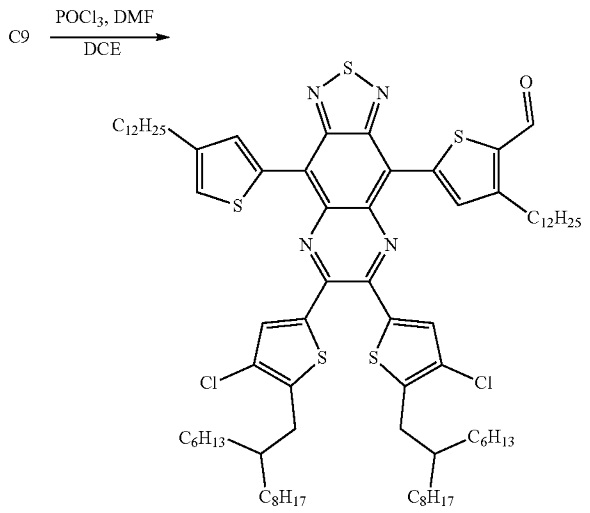

C10

C9 (1.23 g, 0.90 mmol) was placed into a 100 mL three-necked reaction flask. Under nitrogen, 61.5 mL of DCE (1,2-dichloroethane) was added. Under nitrogen, $POCl_3$ (phosphorus oxychloride) (0.503 mL, 5.38 mmol) and DMF (dimethylformamide) (3.47 mL, 4.5 mmol) were mixed and stirred at room temperature for 10 minutes. The above two mixture solutions were mixed and heated to 60° C. with stirring for 15 hours. The reaction was quenched by the addition of 100 mL of water, and 200 mL of DCM was added. The organic layer was extracted three times with 100 mL of water, and the organic layer was dried by adding anhydrous magnesium sulfate and concentrated. The crude product was purified by column chromatography with silica gel, and the eluent was DCM/Hep=5/5. The main segment was collected and concentrated to a dark brown viscous liquid C10. Yield: 1.17 g, 93.2%. $^1H$ NMR (500 MHz, $CDCl_3$) δ 10.19 (s, 1H), 8.80 (s, 1H), 8.77 (s, 1H), 7.47 (s, 1H), 7.46 (s, 1H), 7.37 (s, 1H), 3.11 (m, 2H), 2.80 (m, 6H), 1.80 (m, 6H), 1.30 (m, 84H), 0.85 (m, 18H).

Synthesis of C11

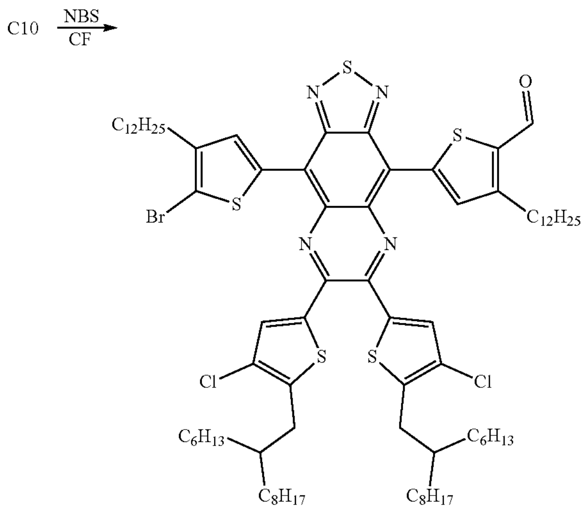

C11

C10 (1.17 g, 0.84 mmol) was replaced into a 100 mL three-neck reaction flask. Under nitrogen, 35 mL of CF was added. Under an ice bath (<10° C.), NBS (N-bromosuccinimide) (0.193 g, 1.08 mmol) was added. The reaction mixture was stirred at room temperature for 18 hours. The organic solvent was removed by a vacuum rotary evaporator. The crude product was purified by column chromatography with silica gel, and the eluent was DCM/Hep=5/5. The main segment was collected and concentrated to a dark brown viscous liquid C11. Yield: 1.22 g, 98.7%. $^1H$ NMR (500 MHz, $CDCl_3$) δ 10.19 (s, 1H), 8.79 (s, 1H), 8.76 (s, 1H), 7.46 (s, 1H), 7.44 (s, 1H), 3.10 (m, 2H), 2.87 (m, 4H), 2.76 (m, 2H), 1.80 (m, 6H), 1.30 (m, 84H), 0.86 (m, 18H).

Synthesis of C13

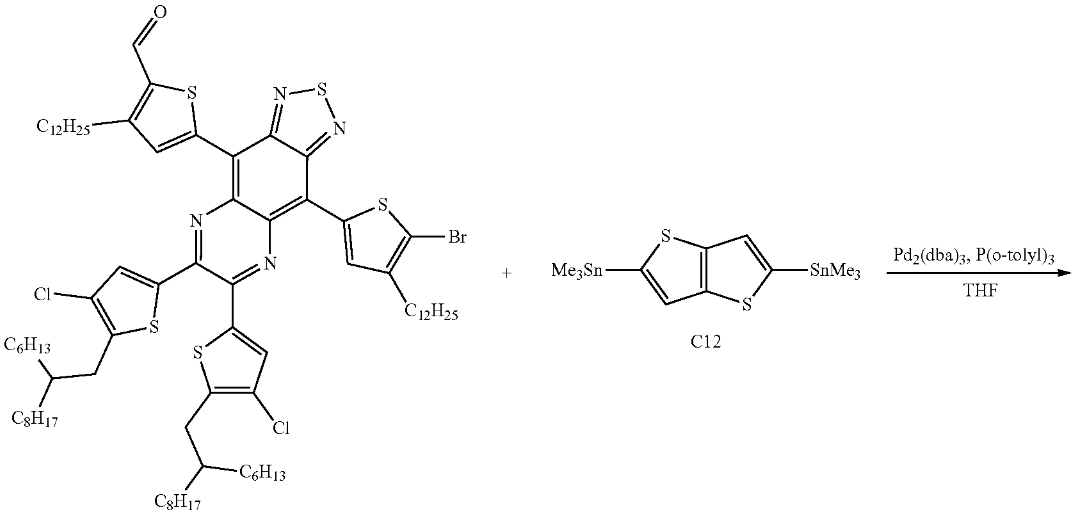

C12

C11

-continued

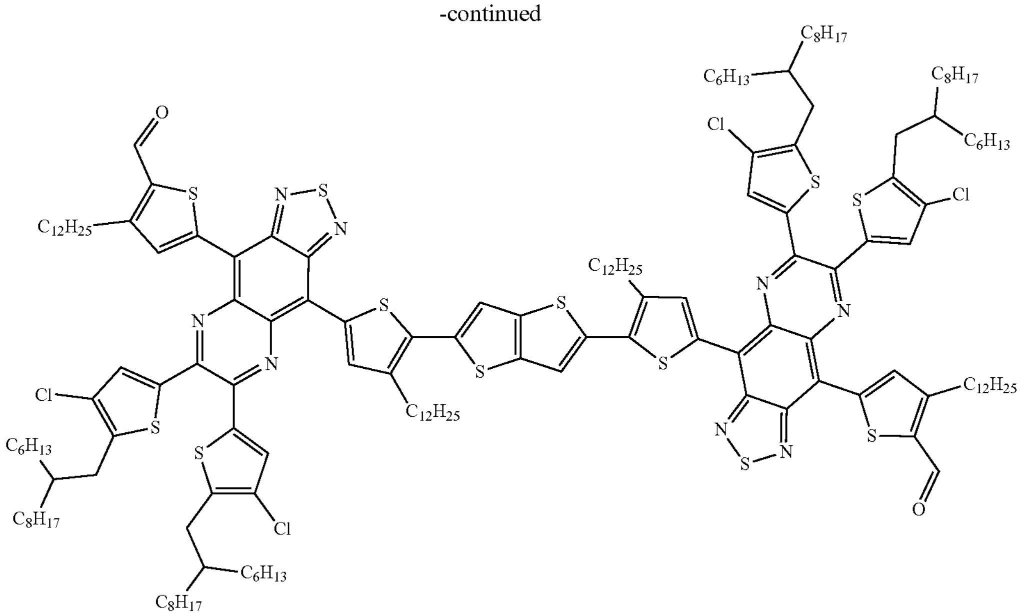

C13

C11 (0.18 g, 0.12 mmol) and C12 (0.028 g, 0.06 mmol) were placed into a 100 mL three-neck reaction flask. 2 mL of THF was added and the reaction mixture was purged with argon for 15 minutes. $Pd_2(dba)_3$ (0.002 g, 0.0024 mmol) and $P(o\text{-tolyl})_3$ (0.003 g, 0.0096 mmol) were added, and the reaction mixture was heated to 66° C. and stirred for 2 hours. After cooling, the reaction mixture was filtered through celite, rinsed with DCM, and the organic solution was removed by a vacuum rotary evaporator. The crude product was purified by column chromatography with 100 g of silica gel, and the eluent was DCM/Hep=5/5. The main segment was collected and concentrated to obtain a brown viscous liquid C13. Yield: 0.14 g, 82.3%. $^1$H NMR (500 MHz, $CDCl_3$) δ 10.18 (s, 2H), 8.90 (s, 2H), 8.72 (s, 2H), 7.59 (s, 2H), 7.47 (s, 2H), 7.44 (s, 2H), 3.10 (m, 4H), 2.87 (m, 8H), 2.76 (m, 4H), 1.80 (m, 12H), 1.30 (m, 168H), 0.84 (m, 36H).

Synthesis of Q1

C13 +

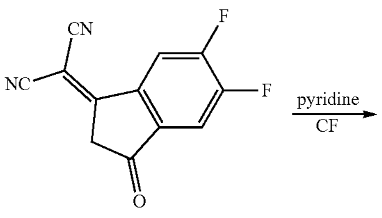

C14

-continued

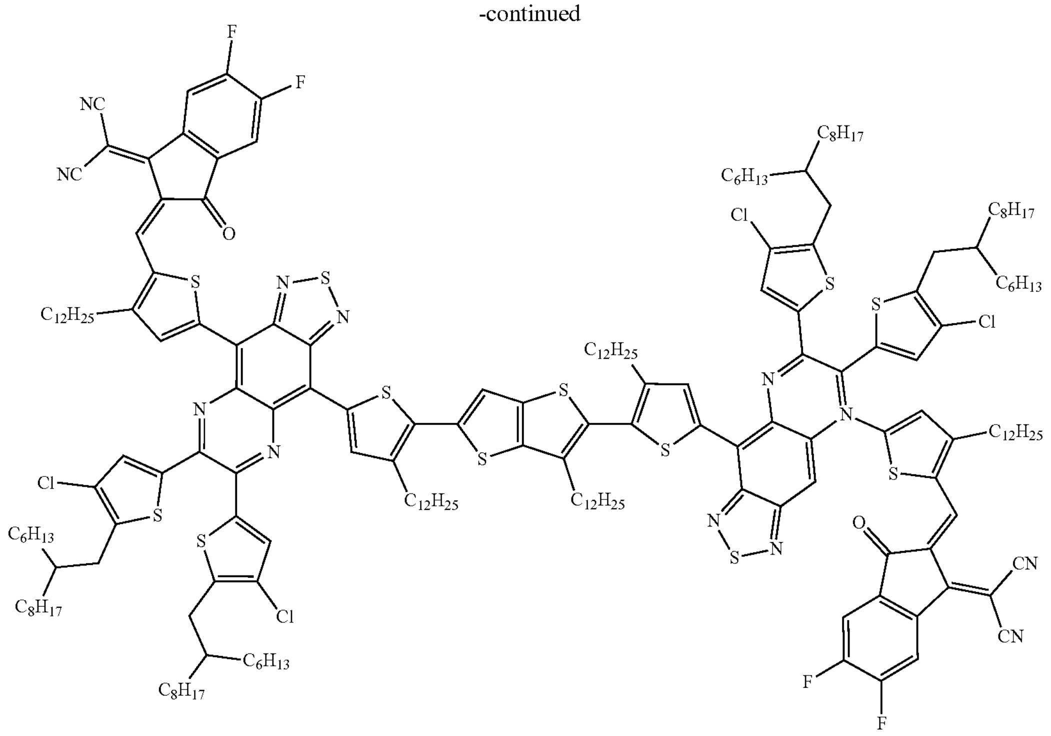

Q1

C13 (0.14 g, 0.047 mmol) and C14 (0.043 g, 0.188 mmol) were added into a 100 mL three-neck reaction flask. Under argon, 2.8 mL of CF (chloroform) was added. Pyridine (0.07 mL, 0.5 V) was added. The reaction mixture was heated to 65° C. with stirring for 2 hours. The reaction was quenched by the addition of 5 mL of MeOH (methanol), and the crude product was precipitated and filtered. The crude product was purified by column chromatography with silica gel, and the eluent was CF/Hep=1/1. The main segment was collected and concentrated to obtain a black solid, which was washed with Acetone and MeOH with ultrasonic vibration, and filtered to obtain a black solid Q1. Yield: 0.135 g, 84.2%. $^1$H NMR (600 MHz, TCE-$d_2$, 100° C.) δ 8.69 (br, 6H), 8.60 (s, 2H), 8.09 (s, 2H), 7.78 (s, 2H), 7.60 (br, 4H), 2.95 (br, 12H), 1.95 (m, 16H), 1.40 (m, 168H), 0.89 (m, 36H).

Synthesis of C16

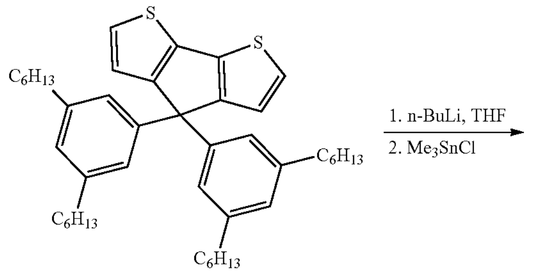

C15

-continued

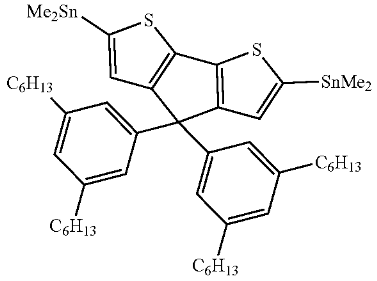

C18

C15 (0.356 g, 0.53 mmol) was added into a 100 mL three-neck reaction flask, and 7 mL anhydrous THF was added. Under an ice bath (<10° C.), n-BuLi (0.96 mL, 2.39 mmol) was added dropwise, and the reaction mixture was stirred for 1 hour. After adding $Me_3SnCl$ (trimethyltin chloride) (0.53 g, 2.66 mmol) dissolved in 2 mL of anhydrous THF, the temperature of the reaction mixture was returned to room temperature. After stirring for two hours, 10 mL of water was added to stop the reaction, and 20 mL of heptane was added. The crude product was extracted three times with 10 mL of water. The organic layer was collected, removed water and concentrated to obtain C16 as a yellow-orange oily liquid. Yield: 0.52 g, 97.4%. $^1$H NMR (500 MHz, $CDCl_3$) δ 7.00 (s, 2H), 6.81 (s, 6H), 2.46 (t, J=7.5 Hz, 8H), 1.50 (br, 8H), 1.26 (br. 24H), 0.86 (m, 12H), 0.35 (m, 18H).

Synthesis of C17

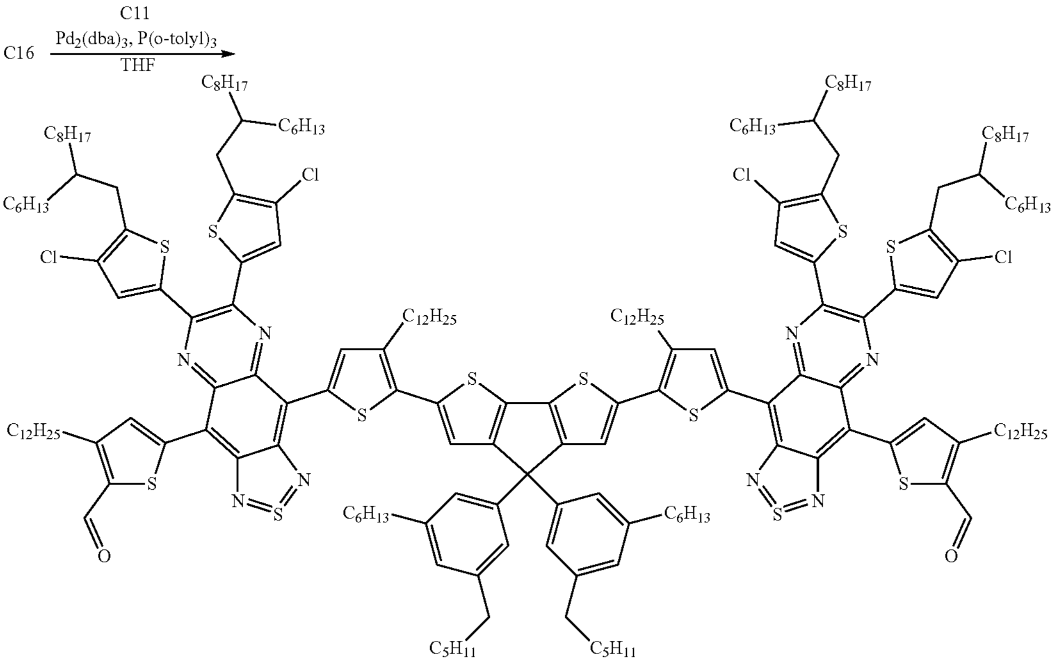

C17

C11 (0.98 g, 0.66 mmol) and C16 (0.328 g, 0.33 mmol) were placed into a 100 mL three-neck reaction flask. 30 mL of THF was added and the reaction mixture was purged with argon for 15 minutes. $Pd_2(dba)_3$ (0.012 g, 0.013 mmol) and $P(o\text{-tolyl})_3$ (0.016 g, 0.052 mmol) were added, and the reaction mixture was heated to 66° C. and stirred for 6 hours. After cooling, the reaction mixture was filtered through celite, rinsed with DCM, and the organic solution was removed by a vacuum rotary evaporator. The crude product was purified by column chromatography with silica gel, and the eluent was DCM/Hep=5/5. The product was further purified by column chromatography with silica gel, and the eluent was toluene/Hep=4/6. The main segment was collected and concentrated to a brown viscous liquid. Yield: 0.9 g, 78.4%. $^1$H NMR (500 MHz, $CDCl_3$) δ 10.19 (s, 2H), 8.94 (s, 2H), 8.80 (s, 2H), 7.60 (s, 2H), 7.48 (s, 2H), 7.31 (s, 2H), 6.97 (s, 4H), 6.95 (s, 2H), 3.10 (m, 4H), 2.97 (m, 8H) 2.83 (m, 4H), 2.52 (m, 8H), 1.95 (m, 16H), 1.30 (m, 196H), 0.80 (m, 48H).

Synthesis of Q2

Synthesis of Q2

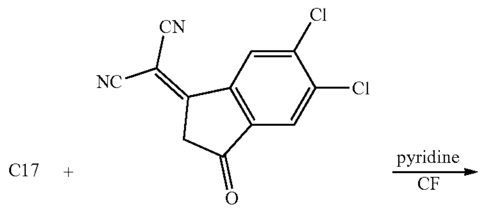

C18

-continued

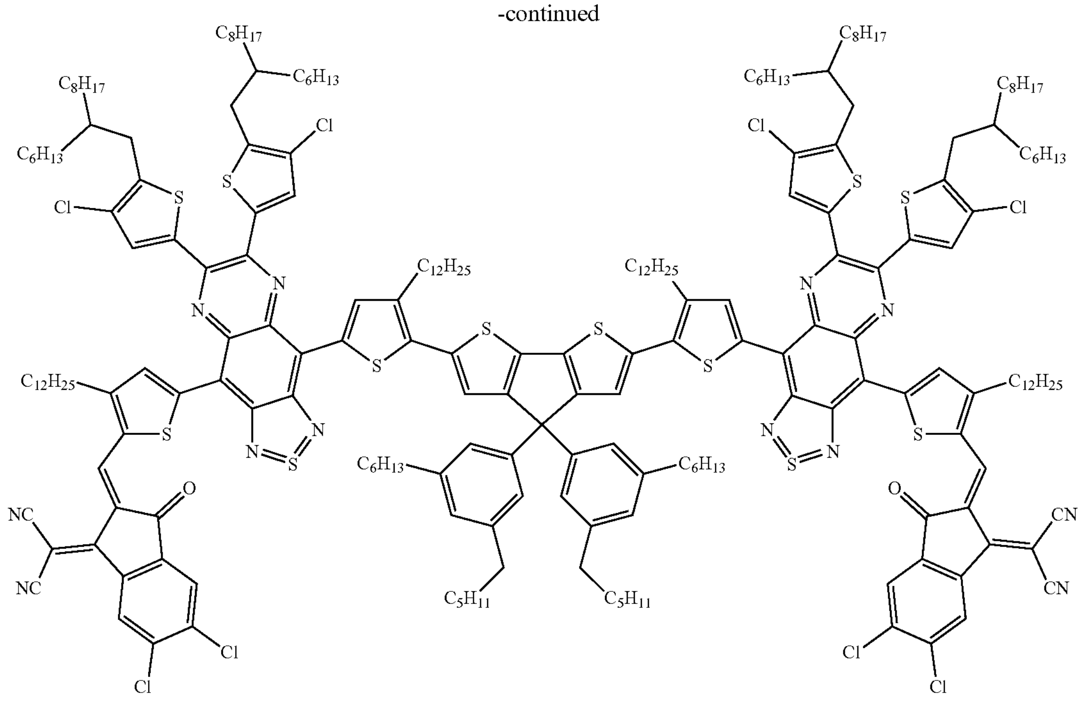

Q2

C17 (0.9 g, 26 mmol) and C18 (0.274 g, 1.04 mmol) were placed into a 100 mL three-neck reaction flask. Under argon, 18 mL of CF was added. Pyridine (0.45 mL, 0.5V) was added. The reaction mixture was heated to 65° C. with stirring for 1.5 hours. The reaction was quenched by the addition of 36 mL of MeOH, and the crude product was filtered. The crude product was wash with EA (ethyl acetate) twice and acetone with ultrasonic vibration, and filtered to obtain a black solid. Yield: 0.91 g, 88.1%. $^1$H NMR (600 MHz, TCE-$d_2$, 100° C.) δ 9.10 (br, 6H), 8.81 (s, 2H), 8.08 (s, 2H), 8.03 (s, 2H), 7.63 (s, 2H), 7.42 (s, 2H), 7.04 (s, 4H), 6.96 (s, 2H), 3.14 (m, 4H), 2.87 (m, 8H), 2.59 (m, 8H), 1.90 (m, 20H), 1.30 (m, 196H), 0.85 (m, 48H).

Synthesis of C20

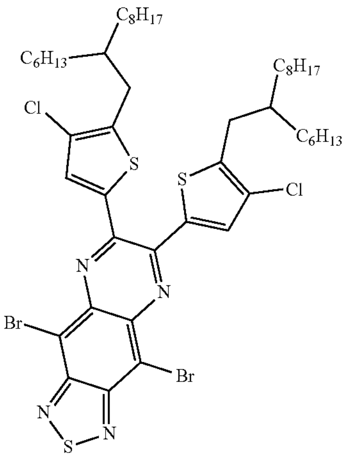

C7

+

-continued

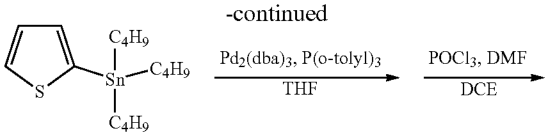

C19

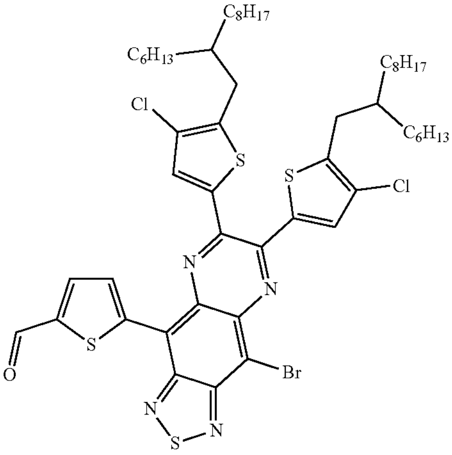

C20

C7 (0.5 g, 0.49 mmol) and C19 (0.121 g, 0.32 mmol) were placed into a 100 mL three-neck reaction flask, and 25 mL of THF was added. The reaction mixture was purged with argon for 15 minutes. $Pd_2(dba)_3$ (0.006 g, 0.007 mmol) and $P(o\text{-tolyl})_3$ (0.008 g, 0.026 mmol) were added, and the reaction mixture was heated to 66° C. and stirred for 2 hours. After cooling down, the reaction mixture was filtered with celite, rinsed with heptane, and the organic solution was removed by a vacuum rotary evaporator. The main part of the intermediate was collected and concentrated to obtain a brown viscous liquid, which was dried in vacuo to obtain 0.21 g. Under nitrogen, 10.5 mL of DCE was added. Under nitrogen, $POCl_3$ (0.114 mL, 1.22 mmol) and DMF (0.79 mL, 10.2 mmol) were combined. The above two mixture solutions were mixed and heated to 60° C. with stirring for 48 hours. The reaction was quenched by the addition of 10 mL of water, and 20 mL of DCM was added. The organic layer was extracted three times with 10 mL of water, and the organic layer was removed by filtration and concentrated with anhydrous magnesium sulfate. The crude product was purified by column chromatography with silica gel, and the eluent was DCM/Hep=1/1. The main segment was collected and concentrated to a dark brown viscous liquid C20. Yield: 0.14 g, 40.8%. $^1$H NMR (500 MHz, $CDCl_3$) δ 10.08 (s, 1H), 8.94 (d, J=4.0 Hz, 1H), 7.92 (d, J=4.0 Hz, 1H), 7.48 (s, 1H), 7.47 (s, 1H), 2.88 (d, J=7.0 Hz, 2H), 2.85 (d, J=7.0 Hz, 2H), 1.83 (m, 2H), 1.29 (m, 48H), 0.84 (m, 12H).

C20 (0.14 g, 0.132 mmol) and C16 (0.07 g, 0.066 mmol) were placed into a 100 mL three-neck reaction flask. Under argon, 4.2 mL of THF was added and the reaction mixture was purged with argon for 15 minutes. $Pd_2(dba)_3$ (0.003 g, 0.003 mmol) and $P(o\text{-tolyl})_3$ (0.004 g, 0.012 mmol) were added, and the reaction mixture was heated to 66° C. and stirred for 2 hours. After cooling, the reaction mixture was filtered through celite, rinsed with DCM, and the organic solution was removed by a vacuum rotary evaporator. The crude product was purified by column chromatography with silica gel, and the eluent was DCM/Hep=1/1. The main segment was collected and concentrated to obtain a brown viscous liquid. C21. Yield: 0.145 g, 79.4%. $^1$H NMR (500 MHz, $CDCl_3$) δ 10.07 (s, 2H), 9.28 (s, 2H), 8.99 (d, J=4.0 Hz, 2H), 7.96 (d, J=4.0 Hz, 2H), 7.51 (s, 2H), 7.45 (s, 2H), 7.16 (s, 4H), 7.16 (s, 2H), 2.94 (m, 4H), 2.78 (m, 4H), 2.50 (m, 8H), 1.81 (m, 4H), 1.30 (m, 16H), 0.85 (m, 124H), 0.73 (m, 24H).

Synthesis of C21

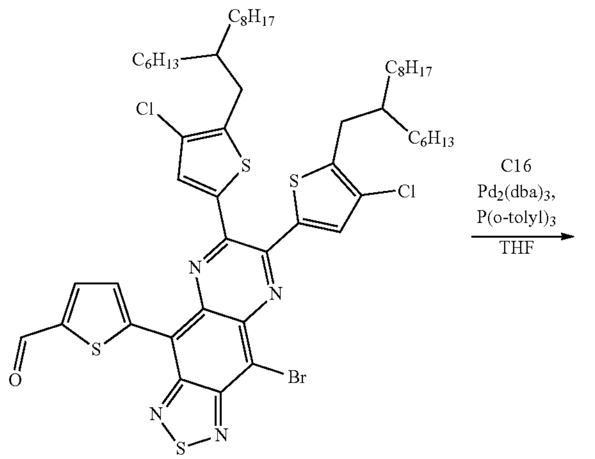

C20

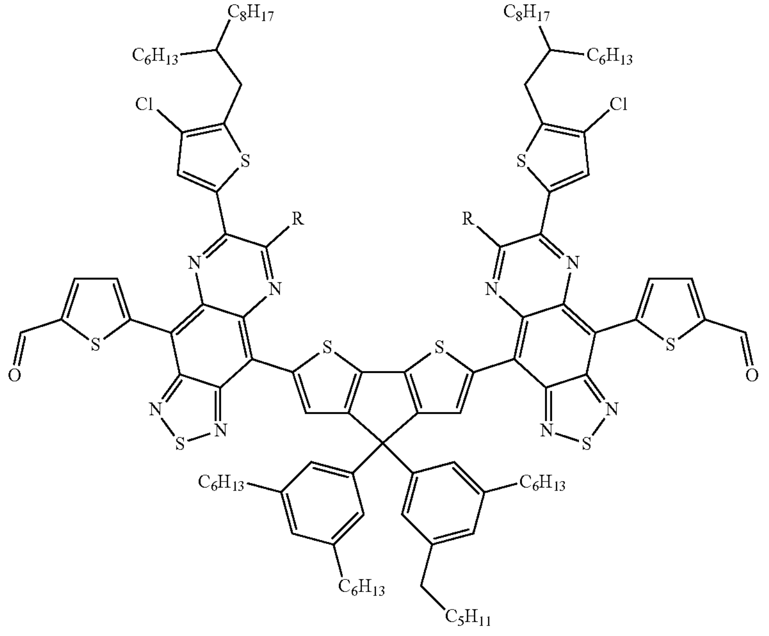

C21

Synthesis of Q3

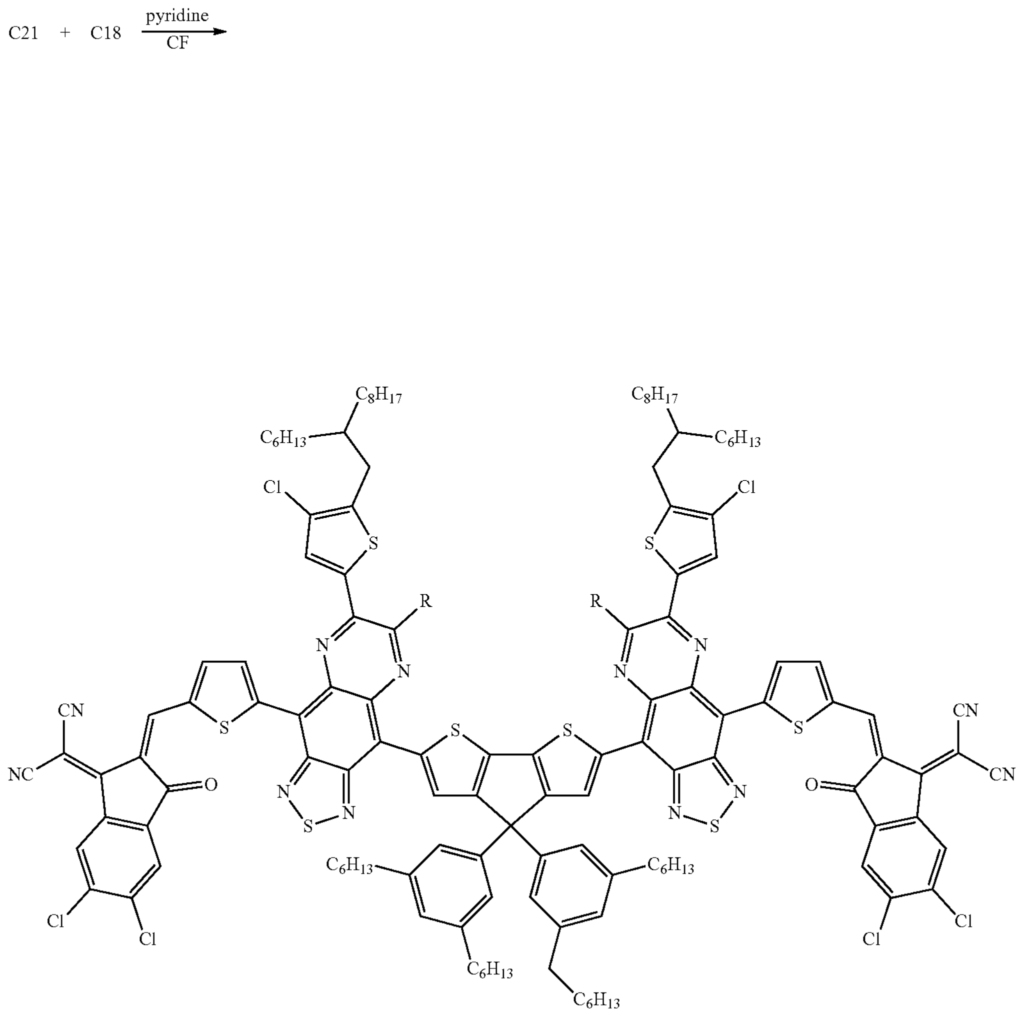

Q3,

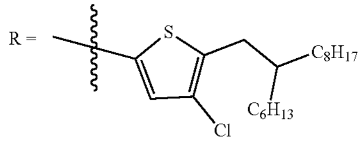

C21 (0.145 g, 0.055 mmol) and C18 (0.058 g, 0.22 mmol) were placed into a 100 mL three-neck reaction flask. Under argon, 2.9 mL of CF was added. Pyridine (0.072 mL, 0.5V) was added. The reaction mixture was heated to 65° C., with stirring for 1.5 hours. The reaction was quenched by the addition of 10 mL of MeOH, and the crude product was filtered and collected. The crude product was purified by column chromatography with silica gel, and the eluent was CF/Hep=8/2. The main segment was collected, concentrated to obtain a black solid, washed with EA with ultrasonic vibration, and filtered to obtain a black solid Q3. Yield: 0.154 g, 89.5%. $^{1}$H NMR (600 MHz, TCE-$d_2$, 100° C.) δ 9.36 (s, 2H), 9.23 (s, 2H), 8.93 (s, 2H), 8.78 (s, 2H), 8.35 (s, 2H), 8.07 (s, 2H), 7.91 (s, 2H), 7.63 (s, 2H), 7.24 (br, 4H), 6.97 (s, 2H), 2.95 (m, 4H), 2.85 (s, 4H), 2.59 (br, 8H), 1.91 (m, 4H), 1.40 (m, 140H), 0.91 (m, 24H).

Synthesis of C23

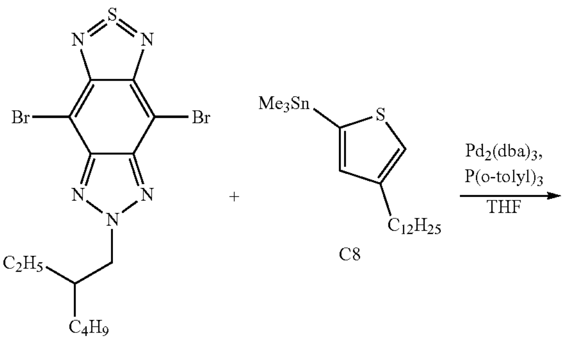

C8

C22

-continued

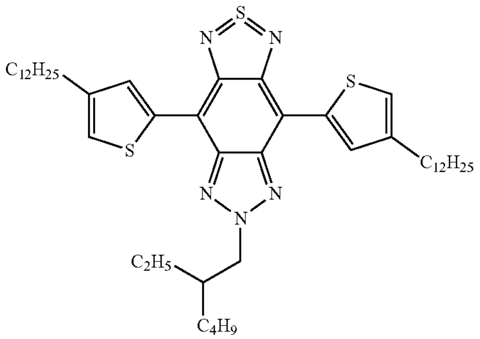

C23

C22 (1 g, 2.23 mmol) and C8 (2.4 g, 5.79 mmol) were placed into a 100 mL three-neck reaction flask, and added 45 mL of THF. The reaction mixture was purged with argon for 15 minutes. $Pd_2(dba)_3$ (0.082 g, 0.089 mmol) and $P(o\text{-tolyl})_3$ (0.108 g, 0.355 mmol) were added, the reaction mixture was heated to 66° C. and stirred for 2 hours. After cooling down, the reaction mixture was filtered with celite, rinsed with heptane, and the organic solution was removed by a vacuum rotary evaporator. The crude product was purified by column chromatography with silica gel, and the eluent was DCM/Hep=1/4. The main segment was collected and concentrated to obtain C23 as a blue solid. Yield: 1.64 g, 93.2%. $^1$H NMR (500 MHz, $CDCl_3$) δ 8.69 (s, 2H), 7.23 (s, 2H), 4.91 (d, J=6.0 Hz 2H), 2.76 (m, 4H), 1.74 (m, 5H), 1.36 (m, 44H), 1.07 (m, 3H), 0.87 (m, 9H).

Synthesis of C24

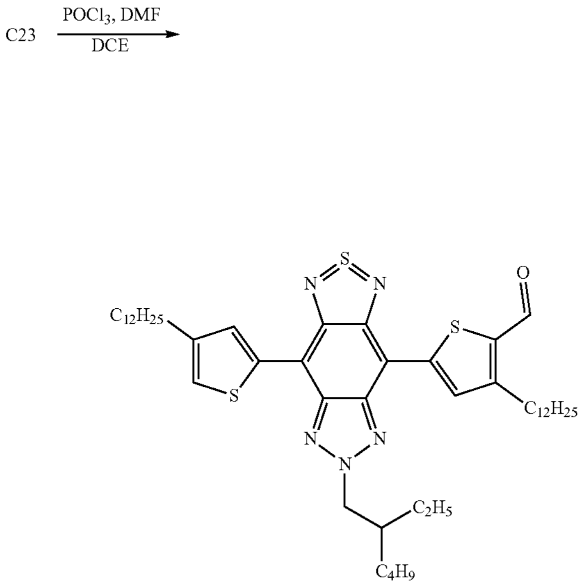

C24

C23 (0.2 g, 0.25 mmol) were placed into a 100 mL three-neck reaction flask, and 10 mL DCE was added under nitrogen. Under nitrogen, $POCl_3$ (0.0234 mL, 0.25 mmol) and DMF (0.155 mL, 2 mmol) were mixed and stirred at room temperature for 10 minutes. At <10° C., the above two mixture solutions were mixed and stirred for 1 hour. The reaction was quenched by the addition of 20 mL of water, and 40 mL of DCM was added. The organic layer was extracted three times with 20 mL of water, and the organic layer was removed by filtration and concentrated with anhydrous magnesium sulfate. The crude product was purified by column chromatography with silica gel, and the eluent was DCM/Hep=1/1. The main segment was collected and concentrated to a blue viscous liquid. Yield: 0.14 g, 67.6%. $^1$H NMR (500 MHz, $CDCl_3$) δ 10.16 (s, 1H), 8.77 (s, 2H), 7.31 (s, 1H), 4.94 (d, J=6.5 Hz, 2H), 3.10 (s, 2H), 2.78 (s, 2H), 1.77 (m, 5H), 1.40 (m, 44H), 1.11 (m, 3H), 0.91 (m, 9H).

Synthesis of C25

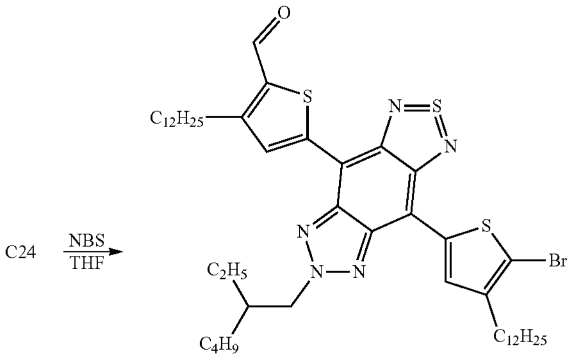

C25

C24 (0.14 g, 0.17 mmol) was placed into a 100 mL three-neck reaction flask, and 7 mL of THF was added under nitrogen. Under an ice bath (<10° C.), NBS (0.030 g, 0.17 mmol) was added. The reaction mixture was stirred at room temperature for 18 hours. The organic solvent was removed by a vacuum rotary evaporator. The crude product was purified by column chromatography with silica gel, and the eluent is DCM/Hep=1/1. The main segment was collected and concentrated to a dark blue solid C25. Yield: 0.15 g, 99.1%. $^1$H NMR (500 MHz, $CDCl_3$) δ 10.16 (s, 1H), 8.77 (s, 1H), 8.63 (s, 1H), 4.93 (d, J=6.5 Hz, 2H), 3.09 (s, 2H), 2.72 (s, 2H), 1.77 (m, 5H), 1.40 (m, 44H), 1.07 (m, 3H), 0.88 (m, 9H).

Synthesis of C26

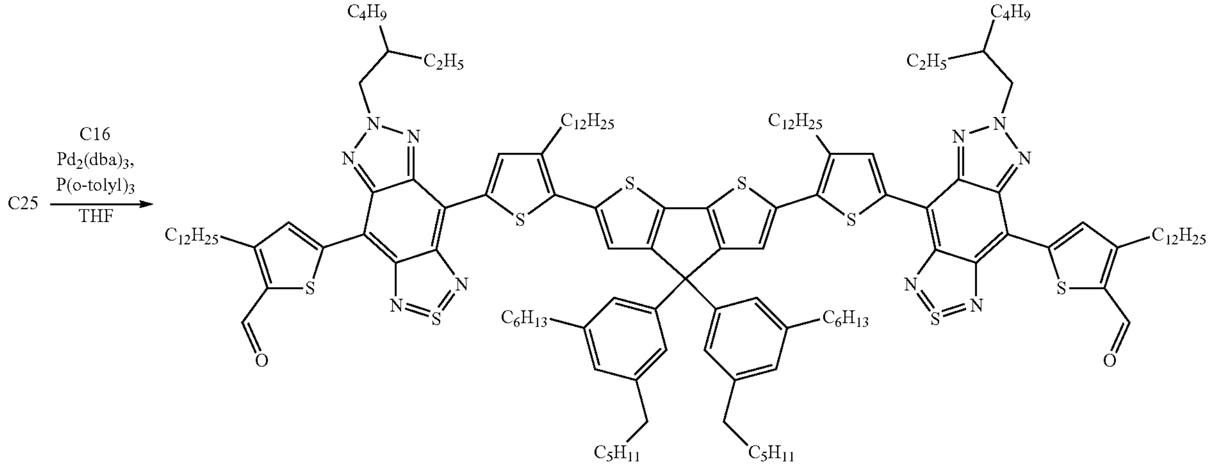

C26

C25 (0.15 g, 0.167 mmol) and C16 (0.083 g, 0.084 mmol) were placed into a 100 mL three-neck reaction flask. 30 mL of THF was added and the reaction mixture was purged with argon for 15 minutes. $Pd_2(dba)_3$ (0.0031 g, 0.0033 mmol) and $P(o\text{-}tolyl)_3$ (0.0041 g, 0.0134 mmol) were added, and the reaction mixture was heated to 66° C. and stirred for 17 hours. After cooling, the crude product was filtered through celite, rinsed with DCM, and the organic solution was removed by a vacuum rotary evaporator. The residue was purified by column chromatography with silica gel, and the eluent is EA:Hep=1:9. The main segment was collected and concentrated to obtain C26 as a black solid. Yield: 0.14 g, 75.5%. $^1H$ NMR (500 MHz, $CDCl_3$) δ 10.16 (s, 2H), 8.80 (s, 2H), 8.75 (s, 2H), 7.30 (s, 2H), 6.95 (s, 4H), 6.92 (s, 2H), 4.94 (m, 4H), 3.09 (m, 4H), 2.94 (m, 4H), 2.53 (m, 8H), 2.02 (m, 2H), 1.85 (m, 8H), 1.28 (m, 120H), 1.10 (m, 6H), 0.85 (m, 30H).

Synthesis of Q4

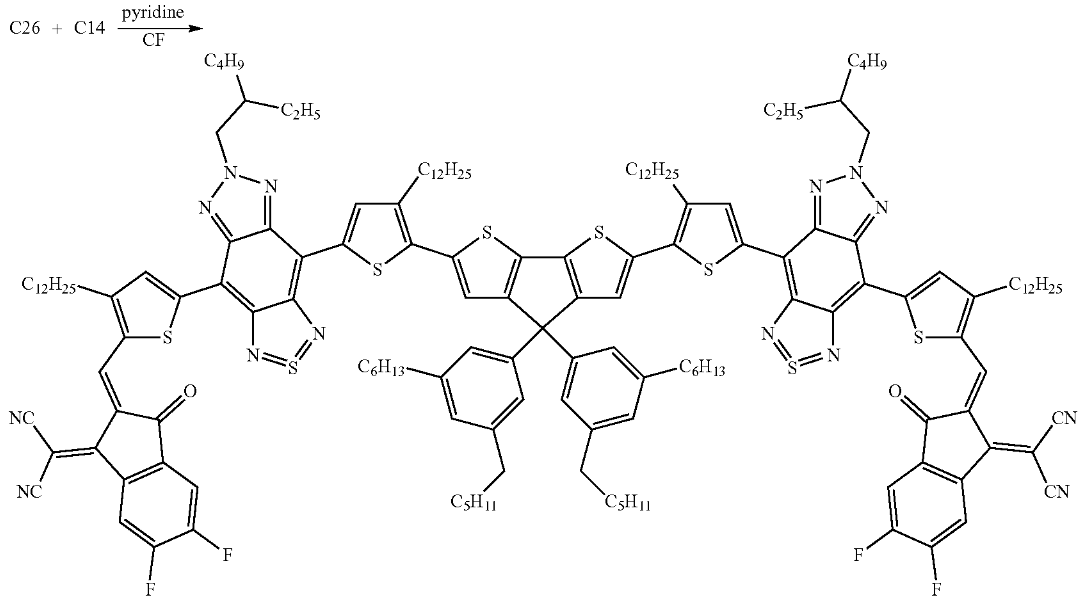

Q4

C26 (0.9 g, 0.26 mmol) and C14 (0.274 g, 1.04 mmol) were placed into a 100 mL three-neck reaction flask. Under argon, 18 mL of CF was added. Pyridine (0.45 mL, 0.5V) was added. The reaction mixture was heated to 65° C. with stirring for 1.5 hours. The reaction was quenched by the addition of 36 mL of MeOH, and the crude product was filtered and collected. The crude product was washed with EA twice and Acetone with ultrasonic vibration, and filtered to obtain black solid Q4. Yield: 0.91 g, 88.1%. $^1H$ NMR (600 MHz, TCE-$d_2$, 100° C.) δ 9.06 (s, 2H), 8.95 (m, 4H), 8.56 (m, 2H), 7.76 (s, 2H), 7.41 (s, 2H). 7.04 (s, 4H), 6.98

(s, 2H), 5.05 (m, 4H), 3.15 (br, 4H), 3.02 (br, 4H), 2.64 (m, 8H), 2.46 (m, 2H), 1.93 (m, 8H), 1.40 (m, 120H), 1.19 (m, 6H), 0.91 (m, 30H).

Characteristic Test of Low Energy Gap Small Molecule Materials Q1, Q2, Q3 and Q4

Figure 2:
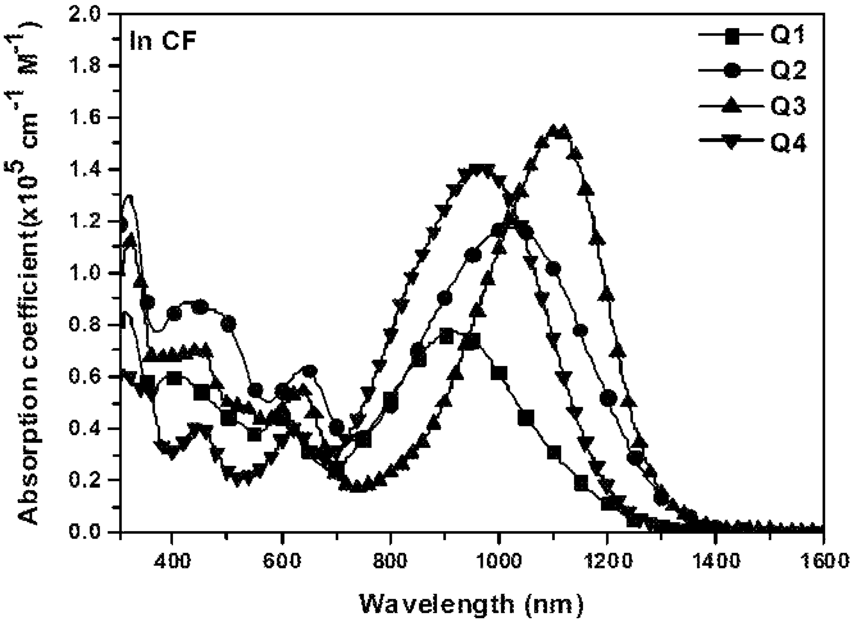
FIG. 2 shows a UV-Vis-NIR absorption spectra of four embodiments Q1 to Q4 of the low energy gap small molecule materials of the present invention dissolved in chloroform solution.
Figure 3:
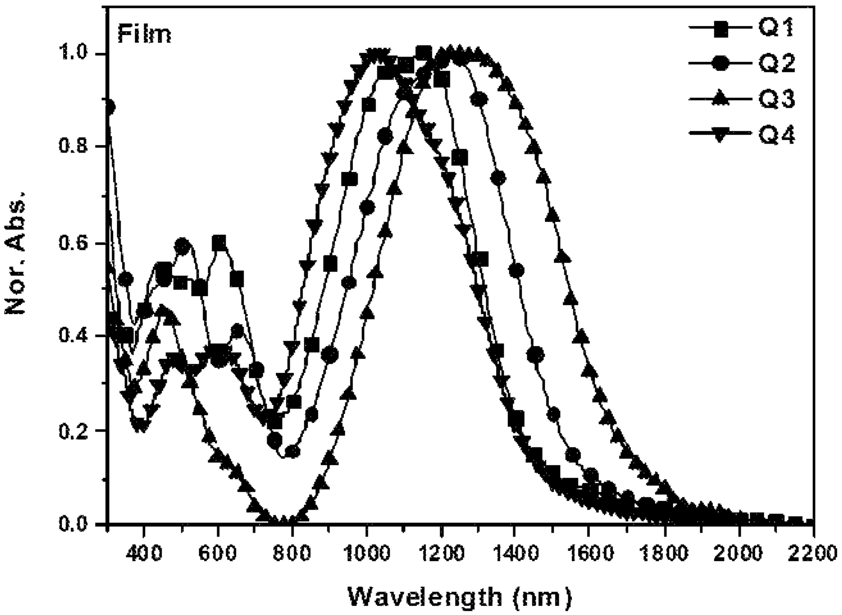
FIG. 3 shows a UV-Vis-NIR absorption spectra of four embodiments Q1 to Q4 of the low energy gap small molecule materials of the present invention in film.
Figure 4:
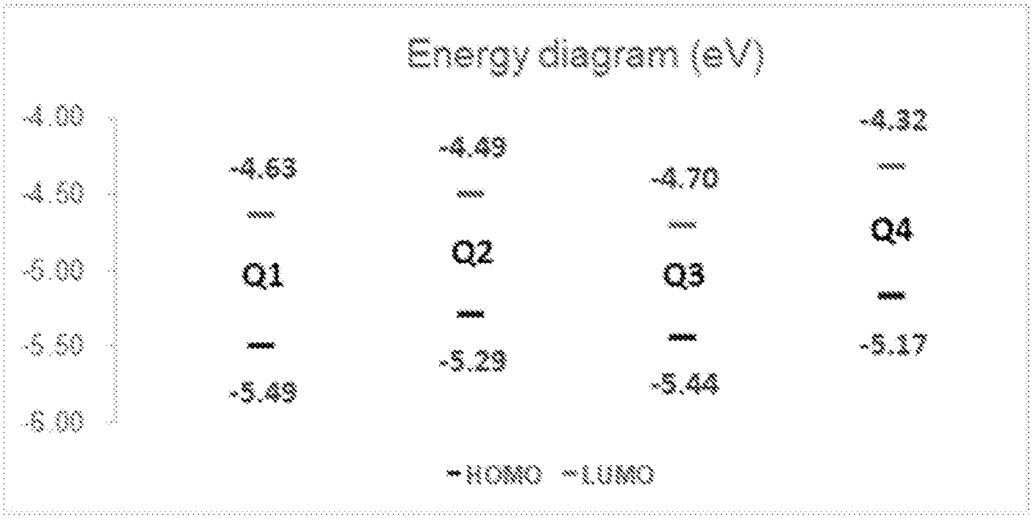
FIG. 4 shows a schematic energy level diagram of four embodiments Q1 to Q4 of the low energy gap small molecule materials of the present invention.

Please refer to FIG. 2 to FIG. 4 and Table 1. FIG. 2 shows a UV-Vis-NIR absorption spectra of four embodiments Q1 to Q4 of the low energy gap small molecule materials of the present invention dissolved in chloroform solution. FIG. 3 shows a UV-Vis-NIR absorption spectra of four embodiments Q1 to Q4 of the low energy gap small molecule materials of the present invention in film. FIG. 4 shows a schematic energy level diagram of four embodiments Q1 to Q4 of the low energy gap small molecule materials of the present invention. Table 1 shows the data results of FIG. 2 to FIG. 4.

TABLE 1 the data results of FIG. 2 to FIG. 4.

| | $\lambda_{soln}^{max}$ (nm) | $\lambda_{film}^{max}$ (nm) | $\lambda_{film}^{onset}$ (nm) | ε ($10^5$ $cm^{-1}$ $M^{-1}$) | $E_g^{opt}$ (eV) | HOMO (eV) | LUMO (eV) | Solubility |
|---|---|---|---|---|---|---|---|---|
| Q1 | 920 | 1160 | 1435 | 0.73 | 0.86 | −5.49 | −4.63 | ○ |
| Q2 | 1025 | 1230 | 1544 | 1.18 | 0.80 | −5.29 | −4.49 | ○ |
| Q3 | 1109 | 1230 | 1689 | 1.54 | 0.74 | −5.44 | −4.70 | ○ |
| Q4 | 965 | 1029 | 1455 | 1.41 | 0.85 | −5.17 | −4.32 | ○ |

As can be seen from FIG. 2, FIG. 3 and Table 1, the low energy gap small molecule material designed in the present invention effectively extends the absorption peak to over 1000 nm, and the maximum absorption coefficients of Q2~Q4 exceed 100,000 $10^5$ $cm^{-1}M^{-1}$ except for Q1. The thin film absorption range of Q1~Q4 (as shown in FIG. 3) show a red shift which is due to the intermolecular stacking effect. Taking Q2 as an example, the maximum absorption peak of the Q2 film is red-shifted by about 200 nm, and it can be predicted that the material can be applied to the organic photodetector with EQE response to 1600 nm. Referring to FIG. 4, the oxidation properties of Q1-Q4 are measured by cyclic voltammetry. The highest occupied molecular orbital (HOMO) is calculated from HOMO=−|4.71÷$E^{xo}$−$E^{ferroncene}$|eV. The optical energy gap $$\left(E_g = 1241/\lambda_{film}^{onset}\text{eV}\right)$$

of the material is known from the absorption onset position $$\left(\lambda_{film}^{onset}\right)$$

of the UV-Vis-NIR absorption spectrum in film state. The lowest unoccupied molecular orbital (LUMO) is calculated from LUMO=HOMO+$E_g$ eV. The energy gaps of the embodiments of the present invention are all less than. 0.9 eV, and the absorption range is over 1000 nm.

In order to confirm whether it can be coated with an environmentally friendly solvent, the solubility measurement in Table 1 is based on whether 8 mg sample in 1 mL o-xylene can be completely dissolved as a standard. Among them, "O" means complete dissolution, and "X" means incomplete dissolution. It can be seen from Table 1 that the low energy gap small molecule materials Q1 to Q4 of the present invention can be completely dissolved in o-xylene. It is proved that the low energy gap small molecule material of the present invention can be coated with o-xylene. In the art, it is an industry trend to use non-halogenated green solvents. Green solvents generally come from renewable resources or can be degraded by soil organisms or other substances, have a short half-life, and are easily decayed into low-toxic and non-toxic substances. Therefore, green solvents are generally less harmful to biological health and the environment than general solvents that are easily chlorinated or highly toxic. Green solvents are also called environmentally friendly solvents. O-xylene is a non-halogen green solvent.

Preparation and Testing of Organic Optoelectronic Devices

A glass coated by a pre-patterned indium tin oxides (ITO) with a sheet resistance of ~15 Ω/sq is used as a substrate. The substrate is ultrasonically oscillated in soap deionized water, deionized water, acetone, and isopropanol in sequence, and washed in each step for 15 minutes. The washed substrate is further treated with a UV-ozone cleaner for 30 minutes. AZO solution (Aluminum-doped zinc oxide) is spin coated on the ITO substrate With a spin rate of 3000 rpm for 40 seconds, and then baked at 120° C. in air for 5 minutes. The active layer solution was prepared in o-xylene. The active layer includes the aforementioned organic semiconductor material. To completely dissolve the active layer material, the active layer solution is stirred on a hot plate at 100° C. for at least 1 hour. Then, the active layer solution is returned to the room temperature for spin coating. Finally, the thin film formed by the coated active layer is annealed at 100° C. for 5 minutes, and then transferred to a thermal evaporation machine. A thin layer (8 nm) of $MoO_3$ is deposited as a hole transporting layer under a vacuum of $3\times10^{-6}$ Torr, and then a silver layer with a thickness of 100 nm is deposited as an upper electrode. All cells are encapsulated with epoxy resin in the glove box to make organic optoelectronic devices (ITO/ETL/active layer/$MoO_3$/Ag).

Figure 5:
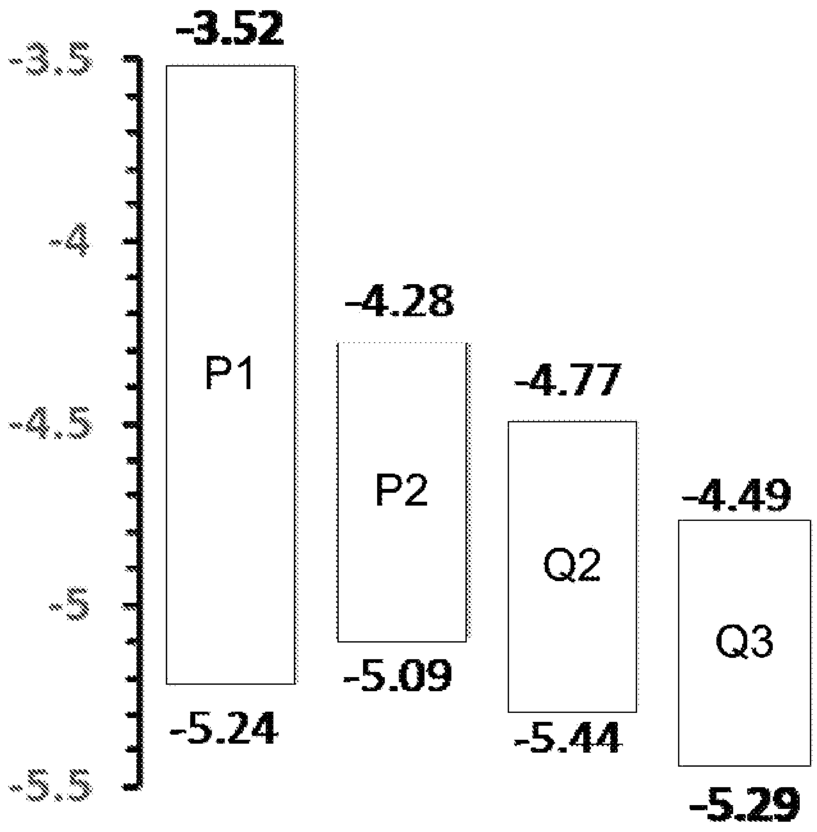
FIG. 5 shows a schematic material energy level diagram of four embodiments P1, P2, Q2 and Q3 of the organic optoelectronic device of the present invention.

Please refer to FIG. 5. FIG. 5 shows a schematic material energy level diagram of four embodiments P1, P2, Q2 and Q3 of the organic optoelectronic device of the present invention. In the preparation of organic optoelectronic devices, P1 or P2 is used as a P-type polymer material, which is configured in combination with the low energy gap small molecule materials Q2 and Q3 of the present invention. The structures of P1 and P2 are as follows:

P1

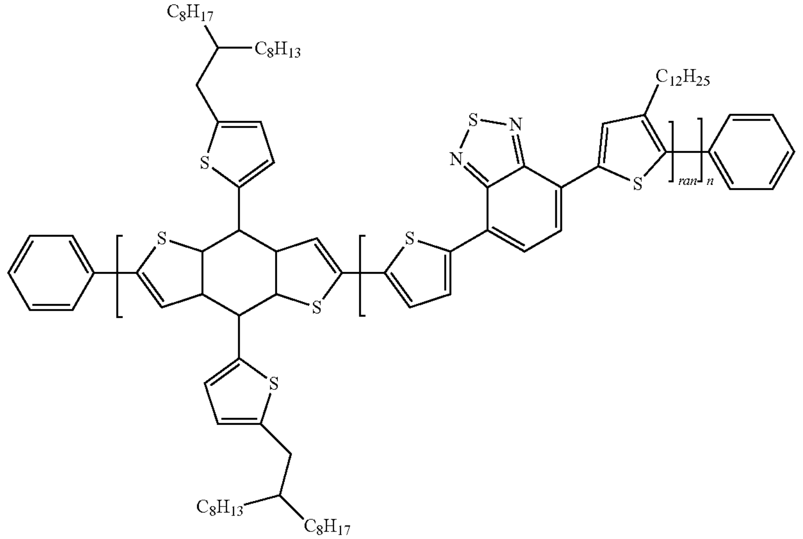

P2

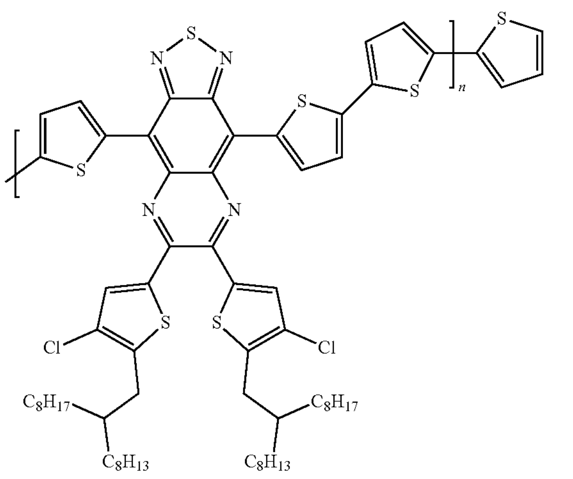

As shown in FIG. 5, for organic optoelectronic devices testing, P2 can be used with Q2 and P1 can be used with Q3. Because the P-type polymer material P2 match with the energy level of Q2, P2 and Q2 have enough driving force in the energy level difference between HOMO and LUMO for excitons dissociation. P1 and Q3 also take this as a collocation principle.

In the preparation of P2:Q2 organic optoelectronic device, the ratio is P2:Q2=1:1, and the concentration is 14 mg/mL in o-xylene. In the preparation of P1:Q3 organic optoelectronic device, the ratio is P1:Q3=1:1, and the concentration is 10 mg/mL in o-xylene. The thickness of the above-mentioned active layer is about 100 nm, and the structures of the organic optoelectronic devices are glass/ITO/AZO/P2:Q2/$MoO_3$/Ag and glass/ITO/AZO/P1:Q3/$MoO_3$/Ag, respectively.

Performance Analysis of Organic Optoelectronic Devices

The performance analysis of the organic optoelectronic device of the present invention is mainly to analyze the external quantum efficiency (EQE) and dark current ($J_d$).

Generally speaking, quantum efficiency (QE) refers to external quantum efficiency (EQE). The quantum efficiency/spectral response reflects the photoelectric conversion efficiency of organic optoelectronic devices for different wavelengths, that is, the ability to effectively convert photons into electrons when illuminated. The conversion efficiency of organic optoelectronic devices is affected by its own material, process, structure and other factors, so that different wavelengths have different conversion efficiencies. In organic photodetector applications, the higher the external quantum efficiency (EQE), the better the signal of the organic photodetector.

Dark current ($J_d$), also known as no-illumination current, refers to the current that flows in an optoelectronic device in the absence of light irradiation. In the dark current test, a bias voltage is applied when the organic optoelectronic device is not illuminated. In the application of the organic photodetector, if the generated current is larger, the noise in the organic photodetcor is larger.

Figure 6:
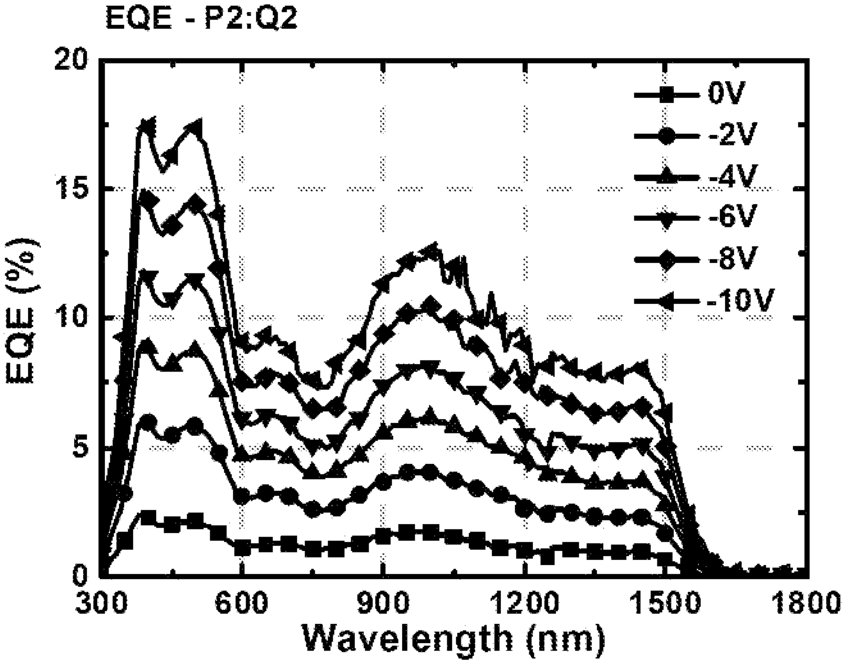
FIG. 6 shows test results of the external quantum efficiency (EQE) of one embodiments P2:Q2 of the organic optoelectronic devices of the present invention.
Figure 7:
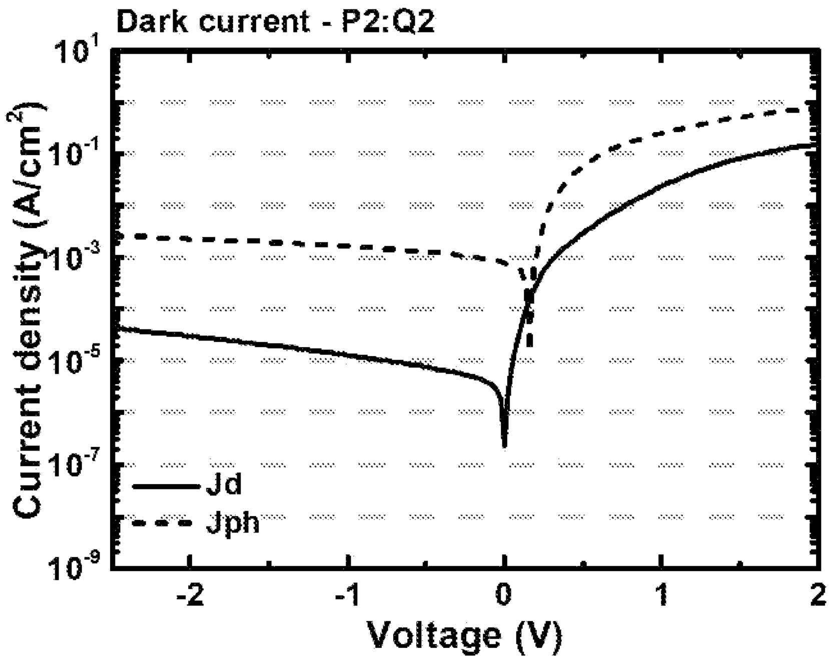
FIG. 7 shows test results of the dark current of the embodiment P2:Q2 of the organic optoelectronic device of the present invention.

Please refer to FIG. 6 and FIG. 7. FIG. 6 shows test results of the external quantum efficiency (EQE) of one embodiments P2:Q2 of the organic optoelectronic devices of the present invention. FIG. 7 shows test results of the dark current of the embodiment P2:Q2 of the organic optoelectronic device of the present invention. As shown in FIG. 6, the EQE results of the organic optoelectronic devices prepared by P2 and Q2 can reach 3.7% under −2 V bias and 12.0% under −10 V bias at 1050 nm; 2.3% under −2 V bias, and 7.9% under −10 V bias at 1350 nm. As shown in FIG. 7, the dark current of the specific embodiment P2:Q2 of the organic optoelectronic device in the present invention is at the level of $10^{-4}$ A/cm$^2$ from −1 V to −2.5 V.

Figure 8:
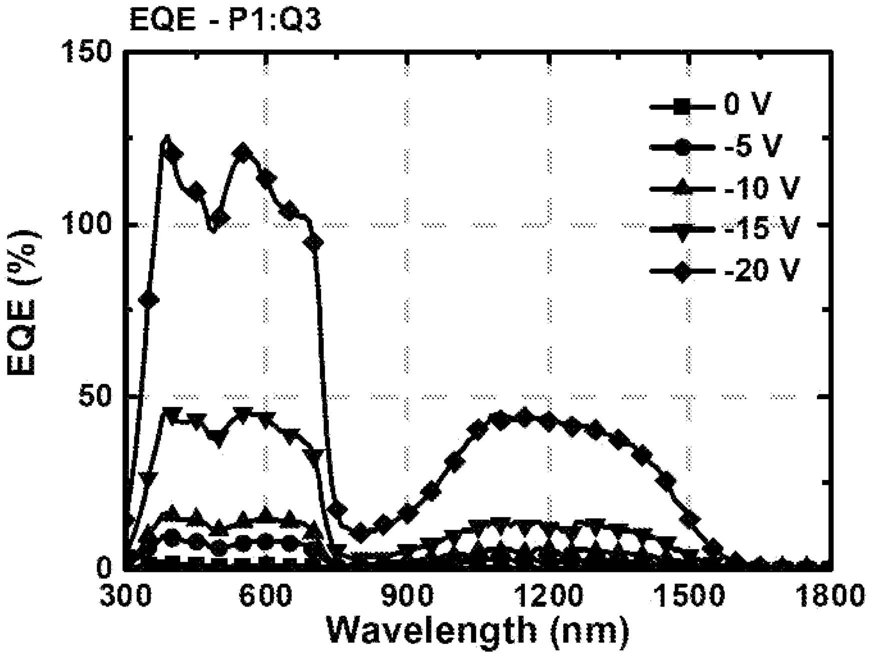
FIG. 8 shows test results of the external quantum efficiency (EQE) of one embodiments P1:Q3 of the organic optoelectronic devices of the present invention.
Figure 9:
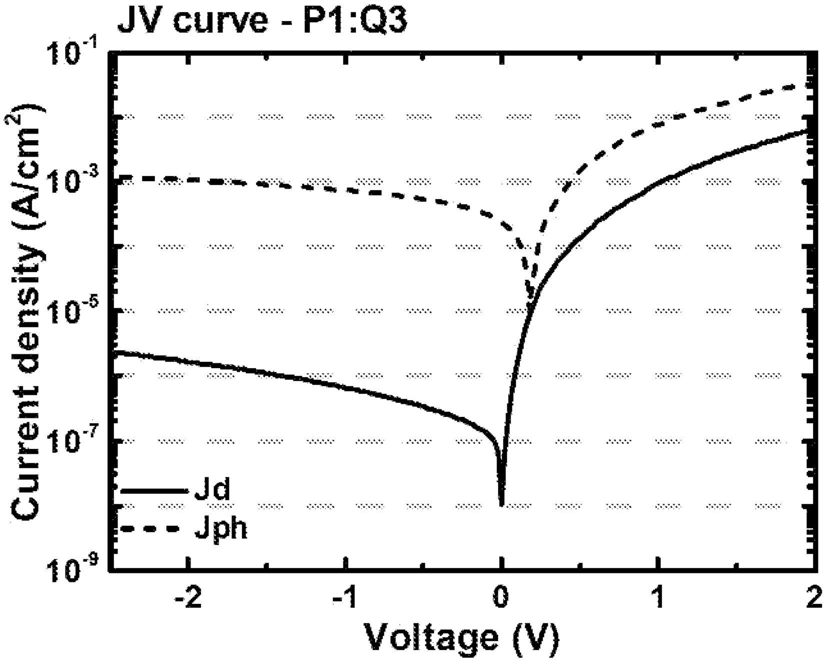
FIG. 9 shows test results of the dark current of the embodiment P1:Q3 of the organic optoelectronic device of the present invention.

Please refer to FIG. 8 and FIG. 9. FIG. 8 shows test results of the external quantum efficiency (EQE) of one embodiments P1:Q3 of the organic optoelectronic devices of the present invention. FIG. 9 shows test results of the dark current of the embodiment P1:Q3 of the organic optoelectronic device of the present invention. As shown in FIG. 8, the EQE results of the organic optoelectronic devices prepared by P1 and Q3 can reach 2.4% under −5 V bias and 40.4% under −20 V bias at 1050 nm; 2.1% under −5 V bias, and 37.5% under −20 V bias at 1350 nm. It can be seen that the organic optoelectronic device prepared by P1:Q3 has an increases in EQE as the bias voltage increases. This phenomenon represents that the organic optoelectronic device prepared by P1:Q3 has the effect of photomultiplier. As shown in FIG. 9, the dark current is expressed at the level of $10^{-7}$ A/cm$^2$ at −1 V, and at the level of $10^{-6}$ A/cm$^2$ from −2 V to −2.5 V.

TABLE 2 specific embodiments of the organic optoelectronic devices of the present invention P2:Q2 and P1:Q3, comparison with the prior art

| | | | | | |
|---|---|---|---|---|---|
| Wavelength (nm) | 1050 | 1050 | 1050 | 1050 | 1050 |
| ATL | DCSQI: PCGBM | DPP-DTT: IR dye | P-fused + $PC_{61}BM$ | P2:Q2 | P1:Q3 |
| Thickness (nm) | 65 | 200 | <200 | 100 nm | 100 nm |
| Band gap (eV) | 1.14 | — | 0.86 | 0.80 | 0.74 |
| Structure | Inverted | Inverted | Conventional | Inverted | Inverted |
| ETL | TiO2 | ZnO | BCP | AZO | AZO |
| HTL | $MoO_3$ | $MoO_3$ | PEDOT | $MoO_3$ | $MoO_3$ |
| ATL solvent | CF | DCB | CB | o-xylene | o-xylene |
| $J_d$ (A/cm$^2$) | $10^{-5}$ @ −8 V | $10^{-5}$ @ −0.5 V | $10^{-4}$ @ −1 V | $10^{-5}$ @ −2 V | $10^{-6}$ @ -2 V |
| EQE | 32% @ −8 V | 0.5% @ 0 V | 0.01% @ 0 V | 12.0% @ −10 V | 40.4% @ −20 V |
| Ref. | Sci. Technol. Adv. Mater. 22 (2021) 196 | Adv. Sci. 2020,7, 2000444 | Adv. Mater. 2010, 22, 2780-2783 | Present invention | Present invention |

Please refer to Table 2. Compared with the performance of EQE response at 1050 nm reported in the current literature, at 1050 nm, the EQE response of the organic optoelectronic device prepared by P2:Q2 can reach 12.0%, and dark current is $10^{-5}$ A/cm$^2$. The EQE of the organic optoelectronic device prepared by P1:Q3 can reach 40.4% due to the photomultiplier effect, and the dark current is $10^{-6}$ A/cm$^2$. It can be seen that, compared with the prior art, the specific embodiments P2:Q2 and P1:Q3 of the organic optoelectronic device of the present invention have good performances in EQE and dark current. Furthermore, the EQE of the organic optoelectronic device of the present invention can also respond at −10 V and −20 V, which means that the organic optoelectronic device of the present invention has a wide range of voltage tolerance. In addition, compared with the prior art, the low energy gap small molecule material developed in the present invention has good solubility in non-halogen solvents, and can use non-halogen solvents (environmentally friendly solvents) for the coating process.

TABLE 3

Specific examples of the organic optoelectronic device of the present invention P2:Q2 and P1:Q3, comparison with the prior art

| | | | | |
|---|---|---|---|---|
| Wavelength (nm) | 1350 | 1350 | 1350 | 1350 |
| ATL | DPP-DTT:1R dye | P-fused + PC BM | P2:Q2 | P1:Q3 |
| Thickness (nm) | 200 | <200 | 100 nm | 100 nm |
| Band gap (eV) | — | 0.86 | 0.80 | 0.74 |
| Structure | Inverted | Conventional | Inverted | Inverted |
| ETL | ZnO | BCP | AZO | AZO |
| HTL | $MoO_3$ | PEDOT | $MoO_3$ | $MoO_3$ |
| ATL solvent | DCB | CB | o-xylene | o-xylene |
| $J_d$ (A/cm$^2$) | $10^{-5}$ @ −0.5 V | $10^{-4}$ @ −1 v | $10^{-5}$ @ −2 V | $10^{-6}$ @ −2 V |
| EQE | 0.9% @0 v | 6.5% @ 0 v | 7.9% @ −10 v | 37.5% @ −20 V |
| Ref. | Adv.Sei. 2020, 7, 2000444 | Adv. Mater. 2010, 22, 2780-2783 | Present invention | Present invention |

Please refer to Table 3. Compared with the performance of EQE response at 1350 nm reported in the current literature, at 1350 nm, the EQE response of the organic optoelectronic device prepared by P2:Q2 can reach 7.9%, and dark current is $10^{-5}$ A/cm$^2$. The EQE of the organic optoelectronic device prepared by P1:Q3 can reach 37% due to the photomultiplier effect, and the dark current is $10^{-6}$ A/cm$^2$. It can be seen that, compared with the prior art, the specific embodiments P2:Q2 and P1:Q3 of the organic optoelectronic device of the present invention have good performances in EQE and dark current. Furthermore, the EQE of the organic optoelectronic device of the present invention can also respond at −10 V and −20 V, which means that the organic optoelectronic device of the present invention has a wide range of voltage tolerance. In addition, compared with the prior art, the low energy gap small molecule material developed in the present invention has good solubility in non-halogen solvents, and can use non-halogen solvents (environmentally friendly solvents) for the coating process.

Based on the above experimental results, in addition to being soluble in non-halogen solvents (environmentally friendly solvents), the low energy gap small molecule material of the present invention has a light absorption range of more than 1000 nm. In addition, the organic optoelectronic devices prepared with this low energy gap small molecule material have good EQE and dark current performance at 1050 nm and 1350 nm.

It should be reminded that, if the substituents in the above description are not clearly stated, the substituents are independently selected from the group consisting of: C1-C30 alkyl, C3-C30 branched alkyl, C1-C30 silyl, C2-C30 ester, C1-C30 alkoxy, C1-C30 alkylthio, C1-C30 haloalkyl, C2-C30 olefin, C2-C30 alkyne, C2-C30 cyano-containing carbon chain, C1-C30 nitro-containing carbon chain, C1-C30 hydroxy-containing carbon chain, C3-C30 keto-containing carbon chain, halogen, cyano and hydrogen.

With the detailed description of the above embodiments, it is hoped that the features and spirit of the present invention can be more clearly described, and the scoped of the present invention is not limited by the embodiments disclosed above. On the contrary, the intention is to cover various changes and equivalent arrangements within the scope of the patents to be applied for in the present invention.

What is claimed is:

1. A low energy gap small molecule material, comprising a structure of Formula I:

(Formula I)

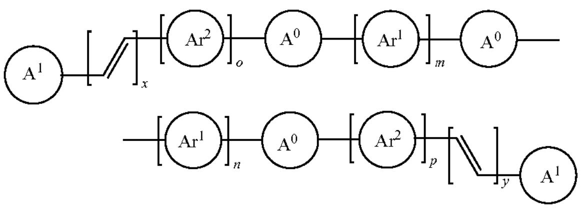

wherein o and p are 1, and m, n, x and y are independently selected from any integer from 0 to 2;

$Ar^0$, $Ar^1$ and $Ar^2$ are electron-donating groups;

$A^0$ is a tricyclic structure with or without substituents, the tricyclic structure containing heteroatom, and the heteroatom comprises at least one of S, N, Si and Se, wherein each $A^0$ in the structure of Formula 1 is independently selected from the group consisting of:

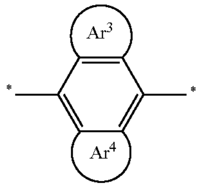

and

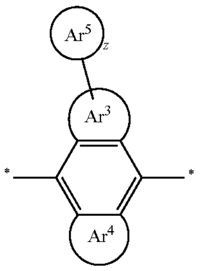

wherein z is any integer from 1 to 8;

$Ar^3$ and $Ar^4$ are independently selected from the group consisting of: aromatic ring with one or more $R^2$ or without substituent, heterocyclic ring with one or more $R^2$ or without substituent, fused ring with one or more $R^2$ or without substituent, fused heterocyclic ring with one or more $R^2$ or without substituent; and $Ar^5$ is independently selected from the group consisting of: C1-C30 alkyl, C3-C30 branched alkyl, C1-C30 silyl, C2-C30 ester, C1-C30 alkoxy, C1-C30 alkylthio, C1-C30 haloalkyl, C2-C30 olefin, C2-C30 alkyne, C2-C30 cyano-containing carbon chain, C1-C30 nitro-containing carbon chain, C1-C30 hydroxy-containing carbon chain, C3-C30 keto-containing carbon chain, halogen, cyano and hydrogen, aromatic ring with one or more $R^3$ or without substituent, heterocyclic ring with one or more $R^3$ or without substituent, fused ring with one or more $R^3$ or without substituent, fused heterocyclic ring with one or more $R^3$ or without substituent;

wherein each of $R^2$ and $R^3$ is independently selected from the group consisting of: C1-C30 alkyl, C3-C30 branched alkyl, C1-C30 silyl, C2-C30 ester, C1-C30 alkoxy, C1-C30 alkylthio, C1-C30 haloalkyl, C2-C30 olefin, C2-C30 alkyne, C2-C30 cyano-containing carbon chain, C1-C30 nitro-containing carbon chain, C1-C30 hydroxy-containing carbon chain, C3-C30 keto-containing carbon chain, halogen, cyano and hydrogen; and $A^1$ is an electron-withdrawing group with or without substituents, and the structure of the electron-withdrawing group comprises at least one of S, N, Si, Se, C═O, —CN and $SO_2$.

2. The low energy gap small molecule material of the claim 1, wherein $Ar^0$, $Ar^1$ and $Ar^2$ are heterocyclic ring containing heteroatom, and the heteroatom comprises at least one of S, N, Si and Se.

3. The low energy gap small molecule material of the claim 1, wherein $Ar^0$, $Ar^1$ and $Ar^2$ in the structure of Formula I are independently selected from the group consisting of the following structures:

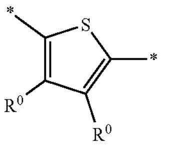

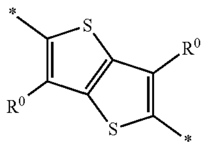

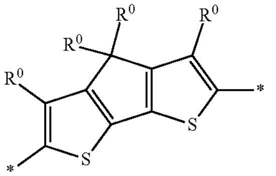

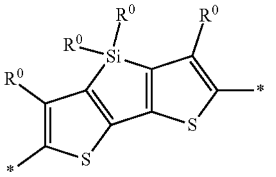

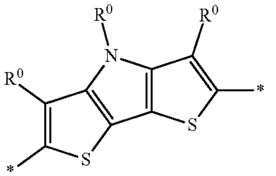

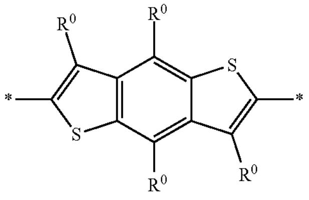

wherein each $R^0$ in each structure is independently selected from the group consisting of: C1-C30 alkyl, C3-C30 branched alkyl, C1-C30 silyl, C2-C30 ester, C1-C30 alkoxy, C1-C30 alkylthio, C1-C30 haloalkyl, C2-C30 olefin, C2-C30 alkyne, C2-C30 cyano-containing carbon chain, C1-C30 nitro-containing carbon chain, C1-C30 hydroxy-containing carbon chain, C3-C30 keto-containing carbon chain, halogen, cyano and hydrogen, aromatic ring with one or more $R^1$ or without substituent, heterocyclic ring with one or more $R^1$ or without substituent, fused ring with one or more $R^1$ or without substituent, fused heterocyclic ring with one or more $R^1$ or without substituent, each of $R^1$ is independently selected from the group consisting of: C1-C30 alkyl, C3-C30 branched alkyl, C1-C30 silyl, C2-C30 ester, C1-C30 alkoxy, C1-C30 alkylthio, C1-C30 haloalkyl, C2-C30 olefin, C2-C30 alkyne, C2-C30 cyano-containing carbon chain, C1-C30 nitro-containing carbon chain, C1-C30 hydroxy-containing carbon chain, C3-C30 keto-containing carbon chain, halogen, cyano and hydrogen.
4. The low energy gap small molecule material of the claim 1, wherein each $A^1$ in the structure of Formula 1 is independently selected from the group consisting of:
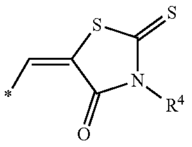
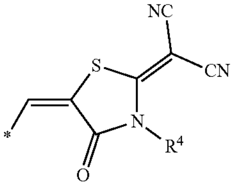
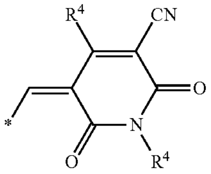
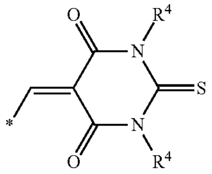
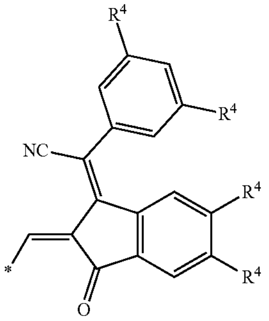
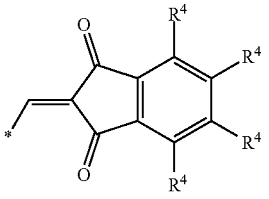
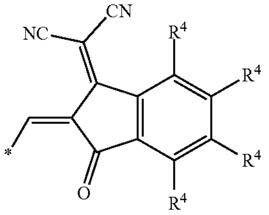
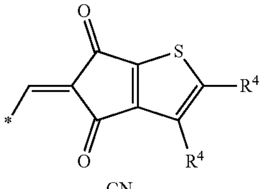
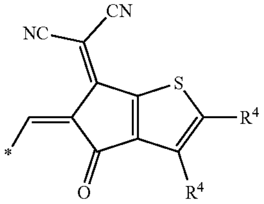
-continued
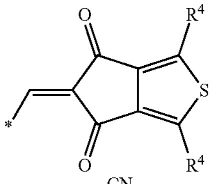
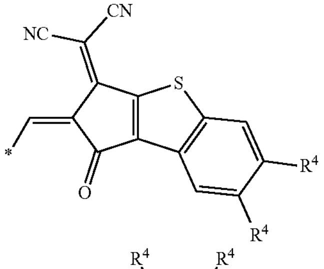
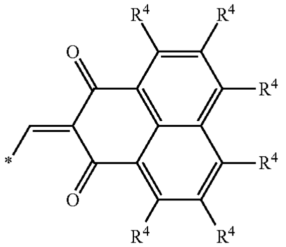
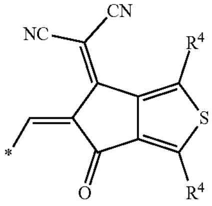
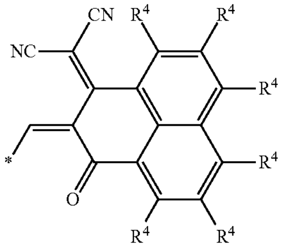
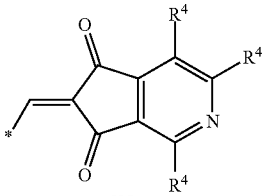
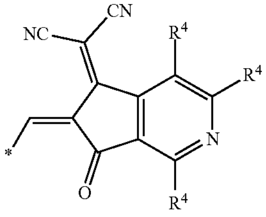
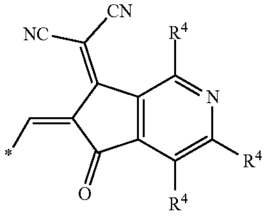

-continued

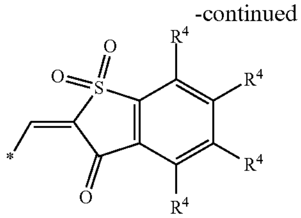

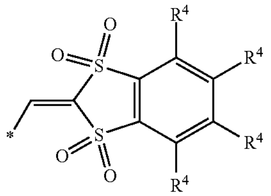

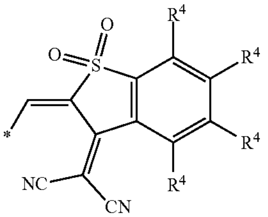

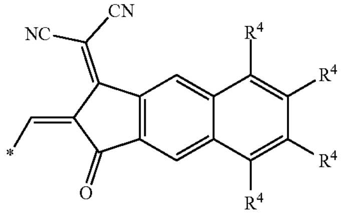

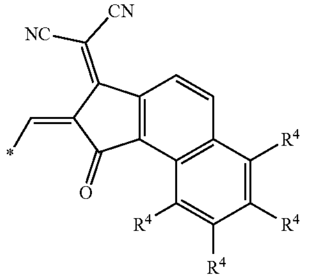

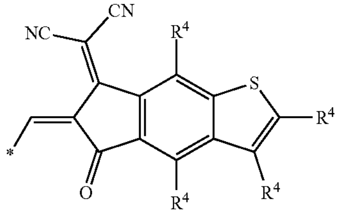

-continued

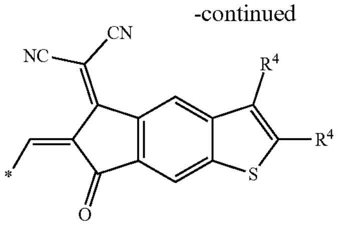

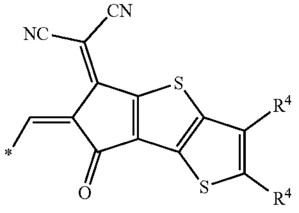

wherein each of $R^4$ is independently selected from the group consisting of: C1-C30 alkyl, C3-C30 branched alkyl, C1-C30 silyl, C2-C30 ester, C1-C30 alkoxy, C1-C30 alkylthio, C1-C30 haloalkyl, C2-C30 olefin, C2-C30 alkyne, C2-C30 cyano-containing carbon chain, C1-C30 nitro-containing carbon chain, C1-C30 hydroxy-containing carbon chain, C3-C30 keto-containing carbon chain, halogen, cyano and hydrogen.

5. The low energy gap small molecule material of the claim 1, wherein m=n, o=p, and x=y in the structure of Formula 1.

6. The low energy gap small molecule material of the claim 1, wherein $Ar^1=Ar^2$ in the structure of Formula 1.

7. The low energy gap small molecule material of the claim 1, wherein $m+n+o+p \neq 0$ in the structure of Formula 1.

8. The low energy gap small molecule material of the claim 1, wherein $x+y \neq 0$ in the structure of Formula 1.

9. An organic optoelectronic device comprising:

a first electrode including a transparent electrode;

a first carrier transport layer;

an active layer which at least comprises a low energy gap small molecule material of the claim 1;

a second carrier transport layer; and a second electrode;

wherein the first carrier transport layer is disposed between the first electrode and the active layer, the active layer is disposed between the first carrier transport layer and the second carrier transport layer, and the second carrier transport layer is disposed between the active layer and the second electrode.

* * * * *